(12) United States Patent
Cunningham et al.

(10) Patent No.: US 7,101,660 B2
(45) Date of Patent: Sep. 5, 2006

(54) METHOD FOR PRODUCING A COLORIMETRIC RESONANT REFLECTION BIOSENSOR ON RIGID SURFACES

(75) Inventors: Brian T. Cunningham, Lexington, MA (US); Jean Qiu, Andover, MA (US)

(73) Assignee: SRU Biosystems, Inc., Woburn, MA (US)

( * ) Notice: Subject to any disclaimer, the term of this patent is extended or adjusted under 35 U.S.C. 154(b) by 670 days.

(21) Appl. No.: 10/196,058

(22) Filed: Jul. 15, 2002

(65) Prior Publication Data

US 2003/0017580 A1    Jan. 23, 2003

Related U.S. Application Data

(63) Continuation-in-part of application No. 10/180,374, filed on Jun. 26, 2002, now Pat. No. 7,023,544, and a continuation-in-part of application No. 10/180,647, filed on Jun. 26, 2002, and a continuation-in-part of application No. 10/059,060, filed on Jan. 28, 2002, and a continuation-in-part of application No. 10/058,626, filed on Jan. 28, 2002, now Pat. No. 6,951,715, and a continuation-in-part of application No. 09/930,352, filed on Aug. 15, 2001.

(60) Provisional application No. 60/303,028, filed on Jul. 3, 2001, provisional application No. 60/283,314, filed on Apr. 12, 2001, provisional application No. 60/244,312, filed on Oct. 30, 2000.

(51) Int. Cl.
*C12Q 1/00*       (2006.01)

(52) U.S. Cl. .................. 435/4; 422/82.11; 435/287.2; 435/288.7; 436/518; 436/531; 436/805

(58) Field of Classification Search ................. None
See application file for complete search history.

(56) References Cited

U.S. PATENT DOCUMENTS 3,689,346 A    9/1972    Rowland .................. 156/245
3,810,688 A    5/1974    Ballman et al. ............. 350/96
3,856,404 A    12/1974   Hershler et al.
3,856,604 A    12/1974   Hershler et al. ........... 156/361
4,009,933 A    3/1977    Firester ...................... 350/152
4,050,895 A    9/1977    Hardy et al. ................ 436/527
4,240,751 A    12/1980   Linnecke et al. ........... 356/409
4,289,371 A    9/1981    Kramer ....................... 350/3.71
4,344,438 A    8/1982    Schultz ....................... 128/633
4,420,502 A    12/1983   Conley ....................... 427/54.1
4,536,608 A    8/1985    Sheng et al. ................ 136/259
4,560,248 A    12/1985   Cramp et al. ................ 385/12
4,576,850 A    3/1986    Martens ...................... 428/156
4,608,344 A    8/1986    Carter et al. ................. 436/34
4,650,329 A    3/1987    Barrett et al. ............... 356/481

(Continued)

FOREIGN PATENT DOCUMENTS

CA    2394966    2/2001

(Continued)

OTHER PUBLICATIONS

Neuschafter et al., "Evanescent resonator chips: a universal platform with superior sensitivity for fluorescent based microarrays", *Biosensors and Bioelectron NICS*, 18(2003)489-497.

(Continued)

*Primary Examiner*—Christopher L. Chin
(74) *Attorney, Agent, or Firm*—McDonnell Boehnen Hulbert & Berghoff LLP

(57)    ABSTRACT

The invention provides a methods for fabricating colorimetric resonant reflection biosensors.

13 Claims, 21 Drawing Sheets

U.S. PATENT DOCUMENTS

| | | | |
|---|---|---|---|
| 4,652,290 A | 3/1987 | Cho et al. | 65/31 |
| 4,668,558 A | 5/1987 | Barber | 428/156 |
| 4,701,008 A | 10/1987 | Richard et al. | 385/132 |
| 4,810,658 A | 3/1989 | Shanks et al. | 436/172 |
| 4,815,843 A | 3/1989 | Tiefenthaler et al. | 356/128 |
| 4,818,710 A | 4/1989 | Sutherland et al. | 436/527 |
| 4,857,273 A | 8/1989 | Stewart et al. | 436/82 |
| RE33,064 E | 9/1989 | Carter | 436/34 |
| 4,876,208 A | 10/1989 | Gustafson et al. | |
| 4,882,288 A | 11/1989 | North et al. | 436/525 |
| 4,888,260 A | 12/1989 | Cowan | |
| 4,931,384 A | 6/1990 | Layton et al. | 435/7 |
| 4,952,056 A | 8/1990 | Tiefenthaler | 356/73.1 |
| 4,958,895 A | 9/1990 | Wells et al. | 350/96.12 |
| 4,992,385 A | 2/1991 | Godfrey | |
| 4,999,234 A | 3/1991 | Cowan | 428/156 |
| 5,071,248 A | 12/1991 | Tiefenthaler et al. | 356/128 |
| 5,118,608 A | 6/1992 | Layton et al. | 435/7.1 |
| 5,155,785 A | 10/1992 | Holland et al. | 385/89 |
| 5,156,785 A | 10/1992 | Zdrahala | 264/108 |
| 5,170,448 A | 12/1992 | Ackley et al. | 385/31 |
| 5,175,030 A | 12/1992 | Lu et al. | 428/30 |
| 5,210,404 A | 5/1993 | Cush et al. | 250/216 |
| 5,229,614 A | 7/1993 | Andersson et al. | 250/370.12 |
| 5,242,828 A | 9/1993 | Bergström et al. | 435/291 |
| 5,268,782 A | 12/1993 | Wenz et al. | 359/81 |
| 5,310,686 A | 5/1994 | Sawyers et al. | |
| 5,337,183 A | 8/1994 | Rosenblatt | 359/248 |
| 5,413,884 A | 5/1995 | Koch et al. | 430/5 |
| 5,442,169 A | 8/1995 | Kunz | 250/227.21 |
| 5,455,178 A | 10/1995 | Fattinger | |
| 5,475,780 A | 12/1995 | Mizrahi | 385/37 |
| 5,478,527 A | 12/1995 | Gustafson et al. | |
| 5,478,756 A | 12/1995 | Gizeli et al. | 436/527 |
| 5,492,840 A | 2/1996 | Malmqvist et al. | |
| 5,496,701 A | 3/1996 | Pollard-Knight | 435/7.4 |
| 5,559,338 A | 9/1996 | Elliott et al. | 250/492.1 |
| 5,598,267 A | 1/1997 | Sambles et al. | 356/369 |
| 5,598,300 A | 1/1997 | Magnusson et al. | 359/566 |
| 5,606,170 A | 2/1997 | Saaski et al. | 250/458.1 |
| 5,615,052 A | 3/1997 | Doggett | 359/811 |
| 5,629,214 A | 5/1997 | Crosby | 436/518 |
| 5,631,171 A | 5/1997 | Sandstrom et al. | 436/518 |
| 5,690,894 A | 11/1997 | Pinkel et al. | 422/68.1 |
| 5,691,846 A | 11/1997 | Benson, Jr. et al. | 359/530 |
| 5,732,173 A | 3/1998 | Bylander et al. | 385/49 |
| 5,738,825 A | 4/1998 | Rudigier et al. | |
| 5,768,461 A | 6/1998 | Svetkoff et al. | 385/116 |
| 5,771,328 A | 6/1998 | Wortman et al. | 385/146 |
| 5,792,411 A | 8/1998 | Morris et al. | 264/400 |
| 5,801,390 A | 9/1998 | Shiraishi | 250/559.3 |
| 5,804,453 A | 9/1998 | Chen | 436/518 |
| 5,814,516 A | 9/1998 | Vo-Dinh | |
| 5,814,524 A | 9/1998 | Walt et al. | 436/514 |
| 5,821,343 A | 10/1998 | Keogh | |
| 5,846,843 A | 12/1998 | Simon | 436/527 |
| 5,864,641 A | 1/1999 | Murphy et al. | 385/12 |
| 5,922,550 A * | 7/1999 | Everhart et al. | 435/7.21 |
| 5,925,878 A | 7/1999 | Challener | 250/225 |
| 5,955,335 A | 9/1999 | Thust et al. | |
| 5,955,378 A | 9/1999 | Challener | 436/525 |
| 5,986,762 A | 11/1999 | Challener | 356/375 |
| 5,991,480 A | 11/1999 | Kunz et al. | 385/37 |
| 5,994,150 A | 11/1999 | Challener et al. | 436/518 |
| 5,998,298 A | 12/1999 | Hetherington et al. | |
| 6,035,089 A | 3/2000 | Grann et al. | 385/129 |
| 6,042,998 A | 3/2000 | Brueck et al. | |
| 6,052,213 A | 4/2000 | Burt et al. | 359/237 |
| 6,076,248 A | 6/2000 | Hoopman et al. | 29/527.1 |
| 6,088,505 A | 7/2000 | Hobbs | 385/147 |
| 6,100,991 A | 8/2000 | Challener | 356/445 |
| 6,128,431 A | 10/2000 | Siminovitch | 385/147 |
| 6,146,593 A | 11/2000 | Pinkel et al. | 422/68.1 |
| 6,174,677 B1 | 1/2001 | Vo-Dinh | |
| 6,185,019 B1 | 2/2001 | Hobbs et al. | 359/30 |
| 6,200,737 B1 | 3/2001 | Walt et al. | 430/320 |
| 6,215,928 B1 | 4/2001 | Friesem et al. | 385/37 |
| 6,218,194 B1 | 4/2001 | Lyndin et al. | |
| 6,235,488 B1 | 5/2001 | Tom-Moy et al. | |
| 6,303,179 B1 | 10/2001 | Koulik et al. | |
| 6,316,153 B1 | 11/2001 | Goodman et al. | 430/8 |
| 6,320,991 B1 | 11/2001 | Challener et al. | |
| RE37,473 E | 12/2001 | Challener | 250/225 |
| 6,338,968 B1 | 1/2002 | Hefti | 436/518 |
| 6,340,598 B1 | 1/2002 | Herron et al. | 436/518 |
| 6,346,376 B1 | 2/2002 | Sigrist et al. | 435/5 |
| 6,377,721 B1 | 4/2002 | Walt et al. | 385/12 |
| 6,404,554 B1 | 6/2002 | Lee et al. | 359/576 |
| 6,449,097 B1 | 9/2002 | Zhu et al. | 359/576 |
| 6,558,957 B1 | 5/2003 | Roinestad et al. | |
| 6,570,657 B1 | 5/2003 | Hoppe et al. | |
| 6,579,673 B1 * | 6/2003 | McGrath et al. | 435/5 |
| 6,587,276 B1 | 7/2003 | Daniell | 359/622 |
| 6,661,952 B1 | 12/2003 | Simpson et al. | 385/37 |
| 6,707,561 B1 | 3/2004 | Budach et al. | 356/521 |
| 6,748,138 B1 | 6/2004 | Wang et al. | 385/37 |
| 6,902,703 B1 | 6/2005 | Marquiss et al. | |
| 2002/0018610 A1 | 2/2002 | Challenger et al. | 385/12 |
| 2002/0123050 A1 | 9/2002 | Poponin | |
| 2002/0127565 A1 | 9/2002 | Cunningham et al. | |
| 2002/0135752 A1 | 9/2002 | Sokolov et al. | |
| 2002/0168295 A1 | 11/2002 | Cunningham et al. | |
| 2002/0171045 A1 | 11/2002 | Perraut | |
| 2003/0003599 A1 | 1/2003 | Wagner et al. | |
| 2003/0017580 A1 | 1/2003 | Cunningham et al. | |
| 2003/0017581 A1 | 1/2003 | Li et al. | |
| 2003/0026891 A1 | 2/2003 | Qiu et al. | |
| 2003/0027327 A1 | 2/2003 | Cunningham et al. | |
| 2003/0027328 A1 | 2/2003 | Cunningham et al. | |
| 2003/0032039 A1 | 2/2003 | Cunningham et al. | |
| 2003/0059855 A1 | 3/2003 | Cunningham et al. | |
| 2003/0068657 A1 | 4/2003 | Lin et al. | |
| 2003/0077660 A1 | 4/2003 | Pien et al. | |
| 2003/0092075 A1 | 5/2003 | Pepper | |
| 2003/0113766 A1 | 6/2003 | Pepper et al. | |
| 2003/0148542 A1 | 8/2003 | Pawlak | |
| 2003/0210396 A1 | 11/2003 | Hobbs et al. | 356/416 |
| 2004/0011965 A1 | 1/2004 | Hodgkinson | |
| 2004/0132172 A1 | 7/2004 | Cunningham et al. | |
| 2004/0132214 A1 | 7/2004 | Lin et al. | |
| 2004/0151626 A1 | 8/2004 | Cunningham et al. | |

FOREIGN PATENT DOCUMENTS

| | | |
|---|---|---|
| CA | 2395318 | 2/2001 |
| CA | 2394966 | 8/2001 |
| CA | 2395318 | 8/2001 |
| CH | 669050 A5 | 2/1989 |
| CH | 670521 A5 | 6/1989 |
| EP | 0112721 | 7/1987 |
| EP | 0326219 | 1/1989 |
| EP | 0326291 | 2/1989 |
| EP | 0517777 | 12/1992 |
| EP | 0660924 | 7/1995 |
| FR | 2801977 | 2/1999 |
| FR | 2801977 | 12/1999 |
| GB | 2156970 A | 10/1985 |
| GB | 2227089 | 7/1990 |
| WO | 8100912 | 4/1981 |
| WO | 0075353 | 3/1983 |
| WO | 8402578 | 7/1984 |
| WO | 8607149 | 12/1986 |
| WO | 9008318 | 7/1990 |
| WO | 9113339 | 9/1991 |

| WO | 9204653 | 3/1992 |
| WO | 9221768 | 12/1992 |
| WO | 9314392 | 7/1993 |
| WO | 9503538 | 2/1995 |
| WO | 9857200 | 12/1998 |
| WO | 9909392 | 2/1999 |
| WO | 9909396 | 2/1999 |
| WO | 9954714 | 10/1999 |
| WO | 9966330 | 12/1999 |
| WO | 0023793 | 4/2000 |
| WO | 0029830 | 5/2000 |
| WO | 0104697 | 1/2001 |
| WO | WO 02/061429 | 8/2002 |

OTHER PUBLICATIONS

International Search Report for foreign counterpart application PCT/US01/50723, Sep. 17, 2002.
Haidner, "Zero-Order Gratings Used as an Artificial Distributed Index Medium", Optik, Wissenschaftlich Verlag GmbH, Stuttgart, DE, vol. 89, No. 3, pp. 107-112, 1992.
Peng, et al., "Experimental Demonstration of Resonant Anomalies in Diffraction from two-Dimensional Gratings", Optics Letters, Optical Society of America, vol. 21, No. 9, pp. 549-551, 1996.
Wilson, et al., "The Optical Properties 1-19 of 'Moth Eye' Antireflection Surfaces", Optical ACTA, vol. 29, No. 7, pp. 993-1009, 1982.
Bagnich, et al., "Tunable Optical Filter", SU 1465855, Derwent Publications, English Translation, Abstract Only, Derwent Publications Ltd.
Magnusson, et al., "New Principal for Optical Filters", Appl. Phys. Letters, 61(9) p. 1022-1024 (1992).
Budach, et al., "Generation of Transducers for Fluorescence-based Microarrays with Enhanced Sensitivity and Their Application for Gene Expression Profiling", Analytical Chemistry, 2003 74(11):2571-7.
Nellen, et al., "Integrated Optical Input Grating Couplers as Biochemical Sensors", Sensors and Actuators, 15 (1988) 285-295.
W. Lukosz and K. Tienfenthaler, "Embossing technique for fabricating integrated optical components in hard inorganic waveguiding materials," Optics Letters, vol. 8, pp. 537-539 (1983).
K. Tiefenthaler and W. Lukosz, "Integrated optical switches and gas sensors," Optics Letters, vol. 10, pp. 137-139 (1984).
Chabay, "Optical Waveguides," Analytical Chemistry, vol. 54, pp. 1071A-1080A (1982).
Sutherland et al., "Optical Detection of Antibody-Antigen Reactions at a Glass-Liquid Interface," Clin. Chem., vol. 30, pp. 1533-1538 (1984).
Ronald T. Holm and Edward D. Palik, "Internal-reflection spectroscopy," Laser Focus, vol. 15, pp. 60-65 (Aug. 1979).
N.J. Harrick and George I. Loeb, "Multiple Internal Reflection Fluorescence Spectrometry," Analytical Chemistry, vol. 45, pp. 687-691 (1973).
P.K. Tien, "Light Waves in Thin Films and Integrated Optics," Applied Optics, vol. 10, 2395-2413 (1971).
Dakss, et al., "Grating Coupler for Efficient Excitation of Optical Guided Waves in Thin Films," Applied Physics Letters, vol. 16, pp. 523-525 (1970).
Sutherland et al., "Immunoassays at a Quartz-Liquid Interface: Theory, Instrumentation and Preliminary Application to the Fluorescent Immunoassay of Human Immunoglobulin G," Journal of Immunological Methods, vol. 74, pp. 253-265 (1984).
English translation of CH 670 521 A5.
English translation of CH 669 050 A5.
MacBeath, et al., "Printing Proteins as Microarrays for High-Throughput Function Determination", Science, vol. 289, pp. 1760-1763, 2000.
deWildt, et a., "Antibody arrays for high-throughput screening of antibody-antigen interactions", Nature Biotechnology, vol. 18, pp. 989-994, 2000.
Cunningham, et al., "A plastic colorimetric resonant optical biosensor for multiparallel detection of label-free biochemical interactions", Sensors and Actuators B, 85 (2002) 219-226.
Caruso, et al., "Quartz Crystal Microbalance Study of DNA Immobilization and Hybridization for Nucleic Acid Sensor Development", Analytical Chemistry, vol. 69, No. 11, pp. 2043-2049, 1997.
Hefti, et al, "Sensitive detection method of dielectric dispersions in aqueous-based, surface-bound macromolecular structures using microwave spectroscopy", Applied Physics Letters, vol. 75, No. 12, pp. 1802-1804, 1999.
Wu, et al., "Bioassay of prostate-specific antigen (PSA) using microcantilevers", Nature Biotechnology, vol. 19, pp. 856-860, 2001.
Wasserman, et al., "Structure and Reactivity of Alkylsiloxane Monolayers Formed by Reaction of Alkyltrichlorosilanes on Silicon Substrates", Langmuir, 5, 1074-1087, 1989.
Kallury, et al., "X-ray Photoelectron Spectroscopy of Silica Surfaces Treated with Polyfunctional Silanes", Anal. Chem., 60, 169-172, 1988.
Cunningham, et al., "Colorimetric resonant reflection as a direct biochemical assay technique", Sensors and Actuators B, 81 (2002) 316-328.
Mullaney, et al., "Epitope Mapping of Neutralizing Botulinum Neurotoxin A Antibodies by Phage Display", Infection and Immunity, vol. 69, No. 10, pp. 6511-6514, 2001.
Neuschafer et al., Evanescent resonator chips: a universal platform with superior sensitivity for fluorescence-based microarrays. Biosensors & Bioelectronics, 18 (2003) 489-497.
Budach et al., Generation of transducers for fluorescence-based microarrays with enhanced sensitivity and their application for gene expression profiling. Analytical Chemistry. Jun. 1, 2003;75(11):2571-7.
U.S. Appl. No. 09/929,957, filed Aug. 15, 2001.
U.S. Appl. No. 09/930,352, filed Aug. 15, 2001.
U.S. Appl. No. 10/415,037, filed Oct. 23, 2001.
U.S. Appl. No. 10/399,940, filed Oct. 23, 2001.
U.S. Appl. No. 10/059,060, filed Jan. 28, 2002.
U.S. Appl. No. 10/201,818, filed Jul. 23, 2002.
U.S. Appl. No. 10/237,641, filed Sep. 9, 2002.
U.S. Appl. No. 10/277,908, filed Aug. 26, 2002.
U.S. Appl. No. 10/233,730, filed Sep. 3, 2002.
U.S. Appl. No. 10/180,374, filed Jun. 26, 2002.
U.S. Appl. No. 10/180,647, filed Jun. 26, 2002.
U.S. Appl. No. 10/253,846, filed Sep. 25, 2002.
U.S. Appl. No. 10/196,058, filed Jul. 15, 2002.
U.S. Appl. No. 10/667,696, filed Sep. 22, 2003.
U.S. Appl. No. 10/058,626, filed Jan. 28, 2002.
Statement of Applicants dated May 4, 2004.
Bertoni, et al., "Frequency-Selective Reflection and Transmission by a Periodic Dielectric Layer", IEEE Transactions on Antennas and Propagation, vol. 37, No. 1, pp. 78-83 (1989).
Brundrett, et al., "Normal-incidence guided-mode resonant grating filters: design and experimental demonstration", Optics Letters, vol. 23, No. 9, pp. 700-702 (1998).
Peng, "Polarization-control Components and Narrow-band Filters Based on Subwavelength Grating Structures" 1996.
Lenau, Torben; Material, Silicon Nitride, 1996, 97, 98.
Cerac, Technical publications: Tantalum Oxide, $Ta_2O_5$ for Optical Coating, 2000, Cerac, Inc.
Cunningham et al., Sensors and Actuators B 85; pp. 219-226 (2002).
Cunningham et al., Sensors and Actuators B 81; pp. 316-328 (2002).
Pandey, A. and Mann, M., Nature. 405(6788):837-46 (2000).
Patterson, S.D., Current Opinions in Biotechnology, 11(4):413-8 (2000).
International Search Report for foreign counterpart application PCT/US03/01175.
Cowan, "The Recording and Large Scale Replication of Crossed Holographic Grating Arrays using Multiple Beam Interferometry", SPIE, vol. 503, Application, Theory, and Fabrication of Periodic Structures, pp. 120-129 (1984).
Cowan, "Holographic honeycomb microlens", vol. 24, No. 5, Optical Engineering, pp. 796-802 (1985).

Cowan, et al., "*The Recording and Replication of Holographic Micropatterns for the Ordering of Photographic Emulsion Grains in Film Systems*", vol. 31, No. 3, *J. Imaging Sci.*, pp. 100-107 (1987).

Wang, et al., "*Guided-mode Resonances in Planar Dielectric-Layer Diffraction Gratings*", vol. 7, No.8, *J. Opt. Soc. Am.*, pp. 1470-1474 (1990).

Cowan, "*Aztec Surface-Relief Volume Diffractive Strucutre*", vol. 7, No. 8, *J. Opt. Soc. Am.*, pp. 1529-1544 (1990).

Patel, et al., "*Multiwavelength Tunable Liquid-Crystal Etalon Filter*", vol. 3, No. 7, *IEEE Photonics Technology Letters*, pp. 643+-644 (1991).

Patel, et al., "*Electrically Tunable and Polarization Insensitive Fabry-Perot etalon with a Liquid-Crystal Film*", vol. 58, No. 22, *American Institute of Physics*, pp. 2491-2493 (1991).

Magnusson, et al., "*Direct Optical Immunosensing (Sensitivity and Selectivity)*", *Sensor and Actuators B*, 6, pp. 122-126 (1992).

Wang, et al., "*Theory and Applications of Guided-Mode Resonance Filters*", vol. 32, No. 14, *Applied Optics*, pp. 2606-2613 (1993).

Wang, et al., "*Design of Waveguide-Grating Filters with Symmetrical Line Shapes and Low Sidebands*", vol. 19, No. 12, *Optical Society of America*, pp. 919-921 (1994).

Jin, et al., "*A Biosensor Concept Based on Imaging Ellipsometry for Visualization of Biomolecular Interactions*", 232, *Analytical Biochemistry*, p. 69-72 (1995).

Brecht, et al., "*Optical Probes and Transducers*", vol. 10, *Biosensors & Bioelectronics*, pp. 923-936 (1995).

Magnusson, "*Transmission Bandpass Guided-Mode Resonance Filters*", vol. 34, No. 35, *Applied Optics*, pp. 8106-8109 (1995).

Peng, et al., "*Experiemental Demonstration of Resonant Anomalies in Diffraction from Two-Dimensional Gratings*", vol. 21, No. 8, *Optics Letters*, pp. 549-551 (1996).

Sigal, et al., "*A Self-Assembled Monolayer for the Binding and Study of Histidine-Tagged Proteins by Surface Plasmon Resonance*", vol. 68, No. 3, *Analytical Chemistry*, pp. 490-497 (1996).

Peng, et al., "*Resonant Scattering from Two-Dimensional Gratings*", vol. 13, No. 5, *J. Opt. Soc. Am. A.*, pp. 993-1005 (1996).

Jordan, et al., "*Surface Plasmon Resonance Imaging Measurements of Electrostatic Biopolymer Adsorption onto Chemically Modified Gold Surfaces*", vol. 69, No. 7, *Analytical Chemistry*, pp. 1449-1456 (1997).

Raguin, et al., "*Structured Surfaces Mimic Coating Performance*", *Laser Focus World*, pp. 113-117 (1997).

Lin, et al., "*A Porous Silicon-Based Optical Interferometric Biosensor*", vol. 278, *Science*, pp. 840-843 (1997).

Morhard, et al., *Immobilization of Antibodies in Micropatterns for Cell Detection by Optical Diffraction*, *Sensors and Actuators B* 70, pp. 232-242 (2000).

Jenison, et al., "*Interference-Based Detection of Nucleic Acid Targets on Optically Coated Silicon*", vol. 19, *Nature Biotechnology*, pp. 62-64 (2001).

Cunningham, et al., "U.S. Provisional Appl. No. *Resonant Reflection Microarray*", U.S. Appl. No. 60/244,312, filed Oct. 30, 2000.

Cunningham, et al., "U.S. Provisional Appl. No. *Resonant Reflection Microarray*", U.S. Appl. No. 60/283,314, filed Apr. 12, 2001.

Cunningham, et al., "U.S. Provisional Appl. No. *Resonant Reflection Microarray*", U.S. Appl. No. 60/303,028, filed Jul. 3, 2001.

Hobbs, et al., "*Automated Interference Lithography Systems for Generation of Sub-Micron Feature Size Patterns*", *SPIE*, vol. 3879, pp. 124-135, Sep. 1999.

Cunningham, "*Introduction to Bioanalytical Sensors*", *Techniques in Analytical Chemistry*, pp. 260-291.

Challenger, et al., "*A Multiplayer Grating-Based Evanescent Wave Sensing Technique*", *Elsevier Science B.B.*, pp. 42-46 (2000).

Huber, et al., "*Direct Optical Immunosensing (Sensitivity and Selectivity)*", *Sensors and Actuators B*, 6, pp. 122-126 (1992).

Invitation to Pay Additional Fees in foreign counterpart application PCT/US01/50723.

Liu, et al., "Development of an optical fiber lactate sensor", Mikrochimica Acta, 1999, 131(1-2), pp. 129-135.

*Coming Inc. v. SRU Biosystems, Inc.*, Memorandum Opinion dated Nov. 15, 2005 in the United States District Court for the district of Delaware.

\* cited by examiner

Amine
- Sulfo-succinimidyl-6-(biotinamido)hexanoate (Sulfo-NHS-LC-Biotin)
  - Streptavidin / avidin then biotinylated molecule
- N,N'-disuccinimidyl carbonate (DSC); •-$NH_2$, non-cleavable
- Dimethyl pimelimidate (DMP); •-$NH_2$, non-cleavable
- Dimethyl 3,3'-dithiobispropionimidate (DTBP); •-$NH_2$, cleavable
- 1-Ethyl-3-(3-Dimethylaminopropyl)carbodiimide Hydrochloride (EDC) and N-Hydroxysulfosuccinimide (Sulfo-NHS); •-COOH
- Sulfo-succinimidyl 6-[a-methyl-a-(2-pyridyl-dithio)toluamido] hexanoate (Sulfo-LC-SMPT); •-SH, cleavable
- N-(B-Maleimidopropyloxy)succinimide ester (BMPS)
  - -$SH_2$, non-cleavable
- Sulfo-succinimidyl 4-[N-maleimidomethyl)cyclohexane-1-carboxylate (Sulfo-SMCC); •-SH, non-cleavable Aldehyde
- Directly with aldehyde or first amino then aldehyde
  - -$NH_2$ Ni(II)
- Using Nitrilotriacetic acid (NTA) group, which forms a chelate with Ni(II)
  - His-tagged molecules

Concentric Circle Design

Hexagonal Grating Design

METHOD FOR PRODUCING A COLORIMETRIC RESONANT REFLECTION BIOSENSOR ON RIGID SURFACES

PRIORITY

This application is a continuation-in-part of U.S. application Ser. No. 10/180,374, entitled "Method and Instrument for Detecting Biomolecular Interactions" filed Jun. 26, 2002, now U.S. Pat. No. 7,023,544 and U.S. application Ser. No. 10/180,674, entitled "Method and Apparatus for Detecting Biomolecular Interactions" filed Jun. 26, 2002, which are continuations-in-part of U.S. application Ser. No. 10/059,060, filed Jan. 28, 2002 and U.S. application Ser. No. 10/058,626, filed Jan. 28, 2002, now U.S. Pat. No. 6,951,715, which are continuations-in-part of U.S. application Ser. No. 09/930,352, filed Aug. 15, 2001, which claims the benefit of U.S. provisional application 60/244,312 filed Oct. 30, 2000; U.S. provisional application 60/283,314 filed Apr. 12, 2001; and U.S. provisional application 60/303,028 filed Jul. 3, 2001, all of which are incorporated herein in their entirety.

TECHNICAL AREA OF THE INVENTION

This invention provides methods of producing colorimetric resonant reflection biosensors.

BACKGROUND OF THE INVENTION

Colorimetric resonant reflection biosensors have been fabricated on rigid surfaces, such as glass, using photoresist etch techniques. For example, a high refractive index dielectric thin film is deposited onto a glass substrate. A layer of photoresist is deposited over the dielectric thin film. The photoresist is exposed to light so as to selectively expose regions where the dielectric thin film is to be removed. The glass is immersed into a photoresist chemical developer solution that removes photoresist only from regions where the photoresist was exposed to higher intensity light. The glass substrate is exposed to an etchant (either a wet chemical solution or a dry reactive ion etch process) which removes the dielectric thin material from areas where the photoresist has been developed away. Any remaining photoresist is selectively removed. This glass substrate fabrication process is costly because each individual biosensor must undergo the expensive photolithography and etching procedures.

Another method of producing a colorimetric resonant reflection biosensor comprises spreading a thin layer of epoxy between a rigid "master" template that contains a negative of the desired colorimetric resonant reflection biosensor surface structure onto a flexible sheet of plastic substrate such as polycarbonate or polyester. The epoxy is cured and the plastic sheet with cured epoxy is peeled away from the master template. A high refractive index dielectric material is deposited over the structured plastic sheet. The limitation of the plastic substrate fabrication process is that the "cure and peel" procedure for generating a surface structure replicated within epoxy requires the substrate to be flexible in order to peel the cured structure away from the rigid master (typically implemented as a silicon or glass wafer or a metal film).

Methods of fabricating colorimetric resonant reflection biosensors that avoid expensive photolithography procedures or that do not require the use of flexible substrate materials are needed in the art.

SUMMARY OF THE INVENTION

One embodiment of the invention provides a method for fabrication of a colorimetric resonant reflection biosensor structure. A colorimetric resonant reflection biosensor structure comprises a substrate and a grating comprised of, or coated with, a high refractive index dielectric film or reflective material. A colorimetric resonant reflection biosensor further comprises one or more immobilized specific binding substances on the high refractive index dielectric film. The method comprises applying a liquid or semi-solid material that is capable of being transformed or cured into a flexible solid over a rigid master structure; transforming the liquid or semi-solid material into a flexible master structure, wherein the flexible master structure has the rigid master structure embossed into a first surface of the flexible master structure; peeling the flexible master structure from the rigid master structure; placing the first surface of the flexible master structure onto a liquid or semisolid layer, wherein the liquid or semi-solid layer is on a rigid substrate; transforming or curing the liquid or semi-solid layer into a solid layer; peeling the flexible master structure from the solid layer; and applying a high refractive index dielectric film or reflective material over the solid layer, whereby a colorimetric resonant reflection biosensor structure is fabricated.

One or more specific binding substances can be immobilized to the high refractive index film or reflective material of the colorimetric resonant reflection biosensor structure to fabricate a colorimetric resonant reflection biosensor.

The rigid master structure can be etched into the surface of a silicon or glass wafer. The liquid or semi-solid layer can be epoxy, a polymer, a cement, a solvent free radiation addition polymerizable crosslinkable material or a resin. The crosslinkable material can be an acrylate epoxy urethane based material. The liquid or semi-solid material can be polydimethylsiloxane.

An adhesion-enhancing thin film is placed between the liquid or semi-solid layer and the rigid substrate before the first surface of the flexible master structure is placed on the liquid or semisolid layer. The rigid substrate can be glass, plastic, polymer or epoxy. The liquid or semi-solid layer can be transformed or cured by an electron beam, ultraviolet light or heat.

The flexible master structure can comprise a grating pattern selected from the group consisting of squares, triangles, sinusoidal waves, inverted "u" shapes, lines, circles, ellipses, trapezoids, ovals, rectangles, hexagons, phase-quantized terraced surface relief patterns whose groove pattern resembles a stepped pyramid, and concentric rings. The flexible master structure can comprise a grating pattern having a periodic spacing of between about 0.1 microns to about 2.0 microns. The flexible master structure can comprise a submicron grating pattern and can have a periodic spacing of between about 0.2 microns to about 0.6 microns.

Another embodiment of the invention provides a method of producing a flexible master structure for use in fabricating a colorimetric resonant reflection biosensor. The method comprises applying a liquid or semi-solid material that is capable of being transformed or cured into a flexible master structure over a rigid colorimetric resonant reflection biosensor master structure; transforming or curing the liquid or semi-solid material into a flexible master structure, wherein the flexible master structure has the rigid colorimetric resonant reflection biosensor master structure embossed into a first surface of the flexible master structure; and peeling the flexible master structure from the rigid colorimetric resonant reflection biosensor master structure; whereby a flexible master structure for use in fabricating a colorimetric resonant reflection biosensor is produced.

Even anther embodiment of the invention provides a method for fabrication of a colorimetric resonant reflection biosensor structure. The method comprises placing a colorimetric resonant reflection biosensor flexible master structure onto a liquid or semi-solid layer, wherein the liquid or semi-solid layer is on a rigid substrate, wherein the flexible master structure is pressed into the liquid or semi-solid layer; transforming or curing the liquid or semi-solid layer into a solid layer; peeling the flexible colorimetric resonant reflection biosensor master structure from the solid layer; and applying a high refractive index dielectric film or reflective material over the solid layer, whereby a colorimetric resonant reflection biosensor structure is fabricated.

The method can further comprise the step of immobilizing one or more specific binding substances to the high refractive index dielectric film or reflective material, wherein a colorimetric resonant reflection biosensor is fabricated.

The invention therefore provides low cost methods of fabricating colorimetric resonant reflection biosensors on rigid surfaces.

BRIEF DESCRIPTION OF THE DRAWINGS

FIG. 8 shows three types of surface activation chemistry (Amine, Aldehyde, and Nickel) with corresponding chemical linker molecules that can be used to covalently attach various types of biomolecule receptors to a biosensor;

FIG. 10A shows a biosensor that is incorporated into a microtitre plate. FIG. 10B shows a biosensor in a microarray slide format;

DETAILED DESCRIPTION OF THE INVENTION

Figure 1:
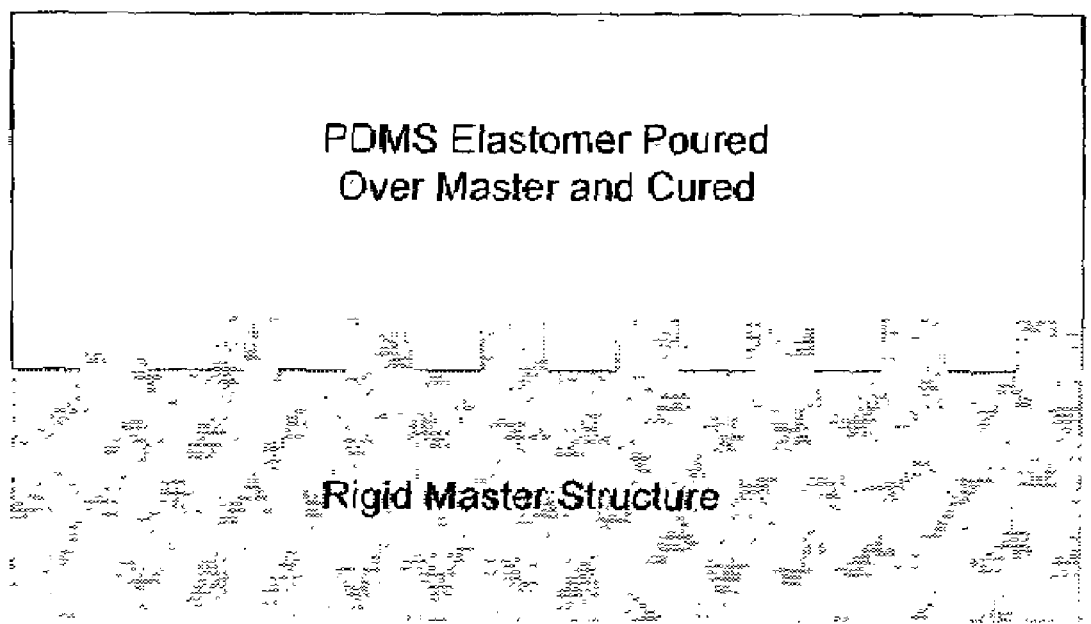
FIG. 1 demonstrates a liquid or semi-solid layer, such as PDMS (polydimethylsiloxane), that has been poured over a rigid master structure which has been etched into a solid surface.

The invention provides methods for making replicated colorimetric resonant reflection biosensor structures on rigid substrate surfaces without the use of photolithography methods or flexible substrates. The methods facilitate low cost manufacturing of colorimetric resonant reflection biosensors into disposable laboratory items made of, for example, glass and plastic, such as microscope slides, microarray slides, petri dishes, and cell culture dishes. For several important applications of colorimetric resonant reflection biosensor technology, such as microarray slides, the most common laboratory format that is typically used with laboratory infrastructure (such as liquid handling dispensers, microarray spotters, incubators, mixers, etc.) involves a rigid substrate. Examples include glass microscope slides, petri dishes, and cell culture plates.

Because these laboratory formats are low cost disposable items, a manufacturing process for embedding colorimetric resonant reflection biosensors into them must also be performed with low cost. The process described in the invention uses an inexpensive flexible cast taken from a master structure to transfer, for example, a sub-micron structured surface to a rigid surface, such as a sheet of glass or plastic.

Methods of Making a Colorimetric Resonant Reflection Biosensor

In general, methods of the invention involve two separate processes. The first process creates a flexible master structure from a rigid master structure. The second process utilizes the flexible master structure to create a colorimetric resonant reflection biosensor structure on a rigid substrate surface.

In one embodiment of the invention, a sub-wavelength surface (SWS) grating is etched into the surface of a rigid master structure such as silicon or glass wafer. Alternatively, a grating can be produced in photoresist. The nonlinear etching characteristics of photoresist are used to develop the exposed film to create a grating pattern. A rigid master structure is then produced from the photoresist. For example, a thin silver film is deposited over the photoresist structure to form a conducting layer upon which a thick film of nickel can be electroplated to form a nickel master plate. The rigid master structure can be formed so as to produce a flexible master structure comprising a grating pattern selected from the group consisting of squares, triangles, sinusoidal waves, inverted "u" shapes, lines, circles, ellipses, trapezoids, ovals, rectangles, hexagons, phase-quantized terraced surface relief patterns whose groove pattern resembles a stepped pyramid and concentric rings. A grating can be a one-, two- or three-dimensional grating. Preferably, the grating is a sub-wavelength structured surface that is capable of functioning as a colorimetric resonant reflection biosensor. Preferably, the flexible master structure comprises a grating pattern having a periodic spacing of between about 0.1 microns to about 2.0 microns. Even more preferably, the flexible master structure comprises a submicron grating pattern, that is, the periodic spacing is less than 1 micron. In one embodiment the periodic spacing is between about 0.2 microns to about 0.6 microns. In another embodiment, the periodic spacing is between about 0.01 microns and about 0.9 microns.

A liquid or semi-solid material that is capable of being transformed to a flexible solid is applied or poured over the rigid master structure so that it conforms to the contours of the rigid master structure surface. Liquid or semi-solid materials include, for example, thermoplastic elastomers such as polydimethylsiloxane (PDMS). The liquid or semi-solid material is cured or transformed by, for example heat, into a flexible solid to form a flexible master structure. The flexible master structure has the rigid master structure embossed into a first surface of the flexible master structure. For example, PDMS can be cured into a flexible solid using heat. The cured or transformed flexible master solid structure is peeled away from the rigid master structure.

A liquid or semi-solid layer material that is capable of being transformed into a solid is applied to a rigid substrate such as glass, plastic, polymer or epoxy to form a liquid or semi-solid material layer. The liquid or semi-solid layer material can be, for example, epoxy, a polymer, a cement, a solvent free radiation addition polymerizable cross linkable material, such as an acrylate epoxy urethane based material, and a resin. An adhesion-enhancing thin film can be applied to the rigid substrate before the liquid or semi-solid layer material is applied to the substrate. Adhesion-enhancing films can comprise, for example, hexamethyldisilane (HMDS).

A flexible master structure has the rigid master structure embossed into a first surface. The first surface of the flexible master structure is applied over the liquid or semi-solid layer material. The flexible master structure is pressed into the liquid or semi-solid layer material, using for example, a roller, to generate a uniformly thin layer of the liquid or semi-solid layer material between the substrate and flexible master structure. The liquid or semi-solid layer material is transformed or cured into a solid layer. The layer material can be cured or transformed by for example, beat, an electron beam, or ultraviolet light. For example, an epoxy layer can be cured using light. The flexible master structure is peeled away from the solid layer. A high refractive index dielectric thin film can be deposited over the transformed or cured solid layer, by, for example, sputter deposition. Specific binding substances can be immobilized on the surface of the high refractive index dielectric thin film to form a colorimetric resonant reflection biosensor.

Colorimetric Resonant Reflection Biosensors

A colorimetric resonant reflection biosensor comprises a subwavelength structured surface (SWS), which is used to create a sharp optical resonant reflection at a particular wavelength that can be used to, for example, track with high sensitivity the interaction of biological materials, such as specific binding substances or binding partners or both. See e.g., U.S. application Ser. Nos. 09/930,352; 10/059,060, and 10/058,626, all of which are incorporated herein in their entirety.

The microreplicating methods of the invention can be used to make a subwavelength structured surface (SWS), such as a colorimetric resonant reflection diffractive grating surface. See U.S. application Ser. Nos. 10/058,626 and 10/059,060. Such a grating surface can be used to create a sharp optical resonant reflection at a particular wavelength that can be used to track with high sensitivity the interaction of biological materials, such as specific binding substances or binding partners or both. The colorimetric resonant reflection diffractive grating surface acts as a surface binding platform for specific binding substances.

Subwavelength structured surfaces are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a one-, two- or three-dimensional grating in which the grating period is small compared to the wavelength of incident light so that no diffractive orders other than the reflected and transmitted zeroth orders are allowed to propagate. A SWS structure can comprise an optical grating sandwiched between a substrate layer and a cover layer that fills the grating. Optionally, a cover layer is not used. When the effective index of refraction of the grating region is greater than the substrate or the cover layer, a waveguide is created. When a filter is designed properly, incident light passes into the waveguide region and propagates as a leaky mode. An optical grating structure selectively couples light at a narrow band of wavelengths into the waveguide. The light propagates only a very short distance (on the order of 10–100 micrometers), undergoes scattering, and couples with the forward- and backward-propagating zeroth-order light. This highly sensitive coupling condition can produce a resonant grating effect on the reflected radiation spectrum, resulting in a narrow band of reflected or transmitted wavelengths. The depth and period of the one-, two- or three-dimensional grating are less than the wavelength of the resonant grating effect.

The reflected or transmitted wavelengths produced by this structure can be modulated by the addition of molecules such as specific binding substances or binding partners or both to the upper surface the grating surface or cover layer. The added molecules increase the optical path length of incident radiation through the structure, and thus modify the wavelength at which maximum reflectance or transmittance will occur.

In one embodiment, a biosensor, when illuminated with white light, is designed to reflect only a single wavelength or a narrow band of wavelengths. When specific binding substances are attached to the surface of the biosensor, the reflected wavelength is shifted due to the change of the optical path of light that is coupled into the grating. By linking specific binding substances to a biosensor surface, complementary binding partner molecules can be detected without the use of any kind of fluorescent probe or particle label. The detection technique is capable of resolving changes of, for example, ~0.1 nm thickness of protein binding, and can be performed with the biosensor surface either immersed in fluid or dried.

A detection system can include, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates and microarray slides. A single spectrometer reading can be performed in several milliseconds; it is thus possible to quickly measure a large number of molecular interactions taking place in parallel upon a biosensor surface, and to monitor reaction kinetics in real time.

This technology is useful in applications where large numbers of biomolecular interactions are measured in parallel, particularly when molecular labels would alter or inhibit the functionality of the molecules under study. High-throughput screening of pharmaceutical compound libraries with protein targets, and microarray screening of protein-protein interactions for proteomics are examples of applications that require the sensitivity and throughput afforded by the compositions and methods of the invention.

Figure 5A:
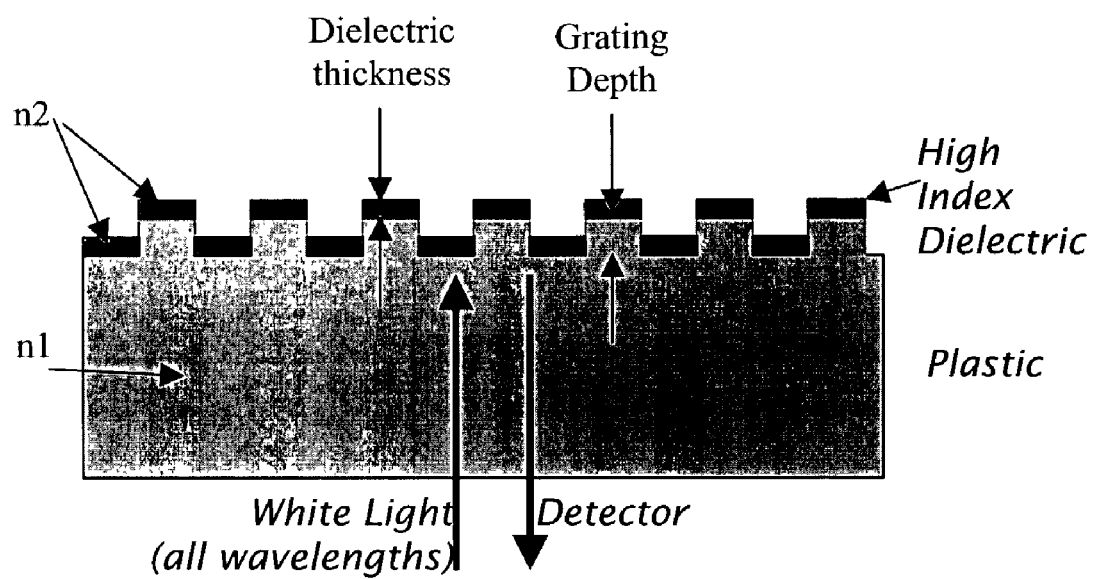
FIG. 5A shows a cross-sectional view of a biosensor wherein light is shown as illuminating the bottom of the biosensor; however, light can illuminate the biosensor from either the top or the bottom.
Figure 5B:
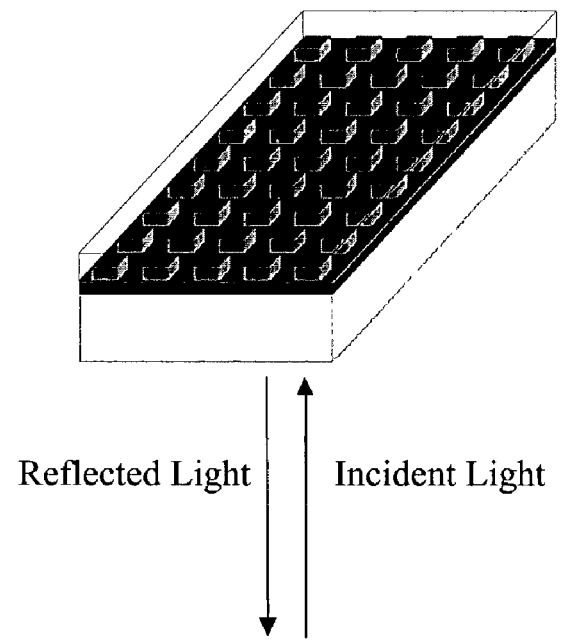
FIG. 5B shows a diagram of a biosensor wherein light is shown as illuminating the bottom of the biosensor; however, light can illuminate the biosensor from either the top or the bottom.

FIGS. 5A and 5B are diagrams of an example of a colorimetric resonant reflection diffractive grating biosensor. In FIG. 5, $n_1$ represents an optical grating. $n_2$ represents the high refractive index layer. Layer thicknesses (i.e. an optional cover layer, one or more specific binding substances, or an optical grating) are selected to achieve resonant wavelength sensitivity to additional molecules on the top surface. The grating period is selected to achieve resonance at a desired wavelength.

A SWS biosensor comprises an optical grating, a substrate layer that supports the grating, and one or more specific binding substances immobilized on the surface of the grating opposite of the substrate layer. Optionally, a cover layer covers the grating surface. An optical grating made according to the invention is coated with a high refractive index dielectric film which can be comprised of a material that includes, for example, zinc sulfide, titanium dioxide, tantalum oxide, and silicon nitride. A cross-sectional profile of a grating with optical features can comprise any periodically repeating function, for example, a "square-wave." An optical grating can also comprise a repeating pattern of shapes selected from the group consisting of lines, squares, circles, ellipses, triangles, trapezoids, sinusoidal waves, ovals, rectangles, and hexagons.

Sensor Characteristics

Figure 6A:
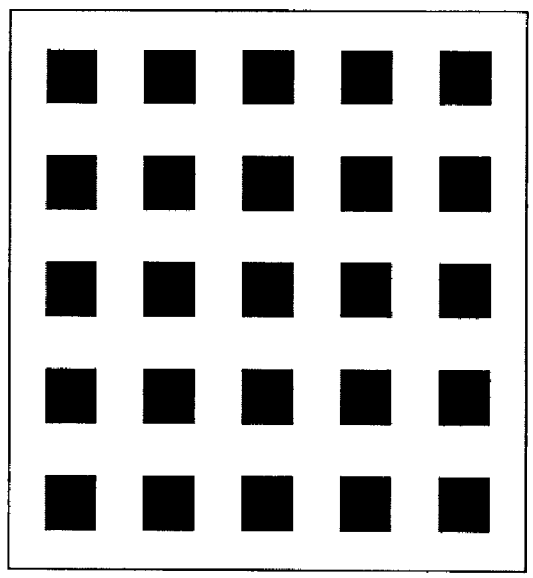
FIGS. 6A–B shows a grating comprising a rectangular grid of squares (FIG. 6A) or holes (FIG. 6B)
Figure 6B:
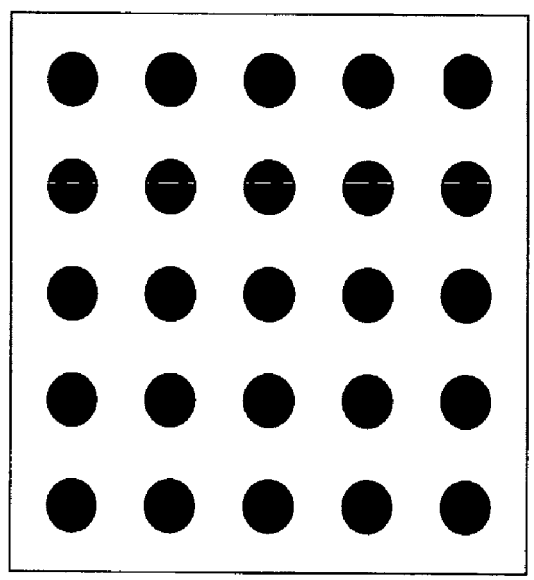
Figure 21:
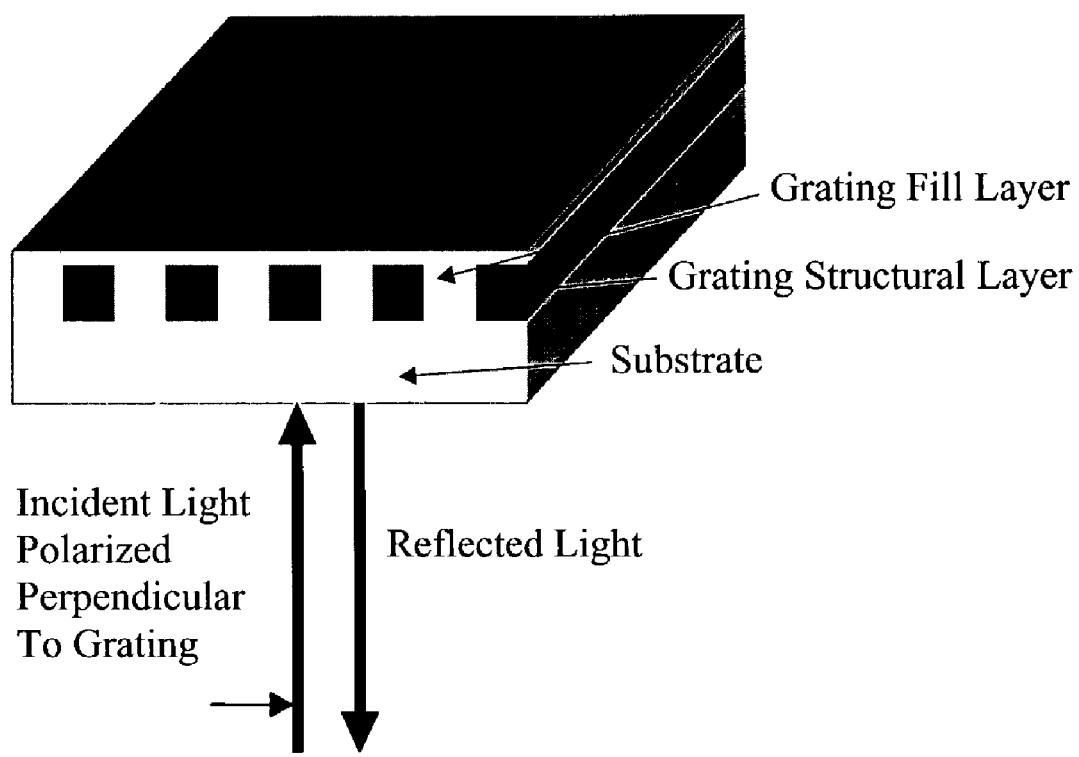
FIG. 21 shows an embodiment of a colorimetric resonant reflection biosensor comprising a one-dimensional grating made according to the methods and compositions of the invention further comprising an optional cover layer.

Linear gratings (i.e., one dimensional gratings) have resonant characteristics where the illuminating light polarization is oriented perpendicular to the grating period. A schematic diagram of a linear grating structure is shown in FIG. 21. A colorimetric resonant reflection biosensor can also comprise, for example, a two-dimensional grating, e.g., a hexagonal array of holes (see FIG. 6B) or squares (see FIG. 6A). Other shapes can be used as well. A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

Figure 7:
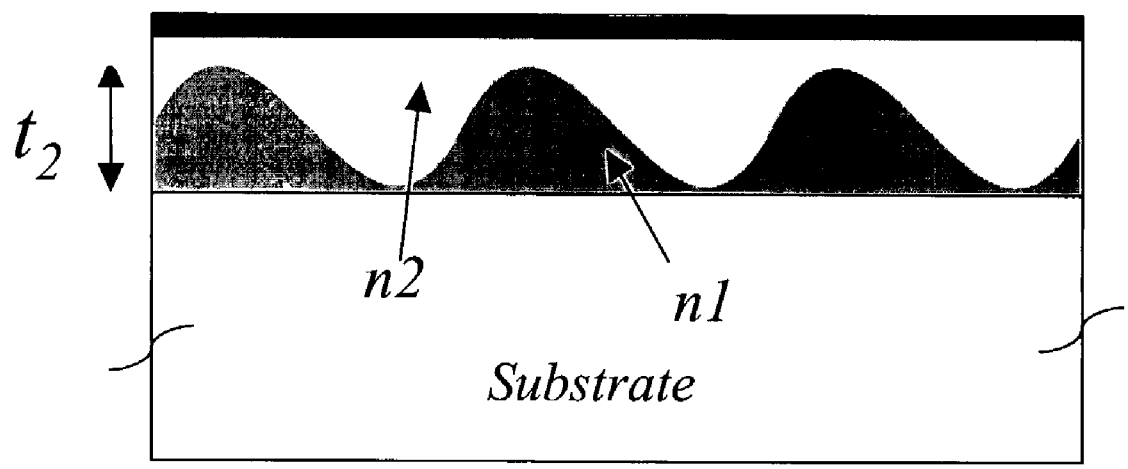
FIG. 7 shows a biosensor cross-section profile utilizing a sinusoidally varying grating profile.

It is also possible to make a resonant biosensor in which the high refractive index material is not stepped, but which varies with lateral position. FIG. 7 shows a profile in which the high refractive index material which coats a two-dimensional grating, $n_1$, is sinusoidally varying in height. $n_2$ represents an optional cover layer, and $t_2$ represents the thickness of the grating. To produce a resonant reflection at a particular wavelength, the period of the sinusoid is identical to the period of an equivalent stepped structure. The resonant operation of the sinusoidally varying structure and its functionality as a biosensor has been verified using GSOLVER (Grating Solver Development Company, Allen, Tex., USA) computer models.

A biosensor of the invention can further comprise a cover layer on the surface of an optical grating opposite of a substrate layer. Where a cover layer is present, the one or more specific binding substances are immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a biosensor of the invention will be illuminated with white light that will contain light of every polarization angle. The orientation of the polarization angle with respect to repeating features in a biosensor grating will determine the resonance wavelength. For example, a "linear grating" (i.e., a one-dimensional grating) biosensor consisting of a set of repeating lines and spaces will have two optical polarizations that can generate separate resonant reflections.

Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor can generally be designed to optimize the properties of only one polarization (the s-polarization), and the non-optimized polarization is easily removed by a polarizing filter.

Figure 17:
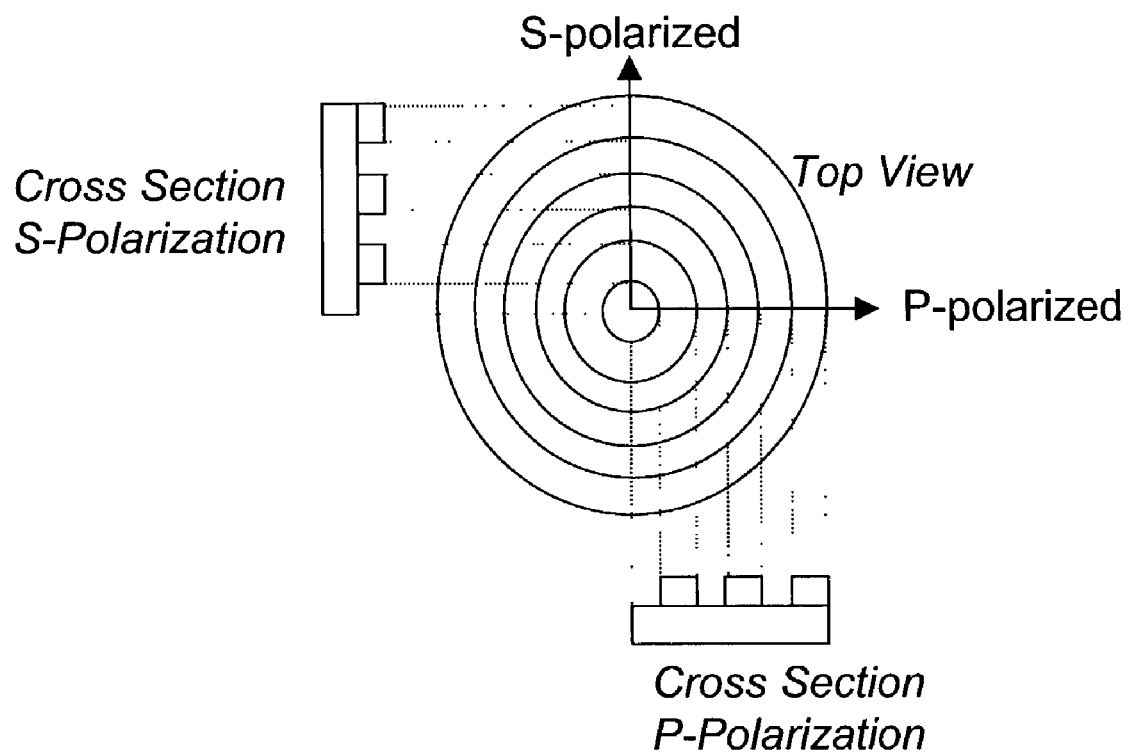
FIG. 17 shows a colorimetric resonant reflection or transmission filter structure consisting of a set of concentric rings.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as a microarray spot or a microtiter plate well. Each separate microarray spot or microtiter plate well has a separate concentric ring pattern centered within it. See, e.g., FIG. 17. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

Figure 18:
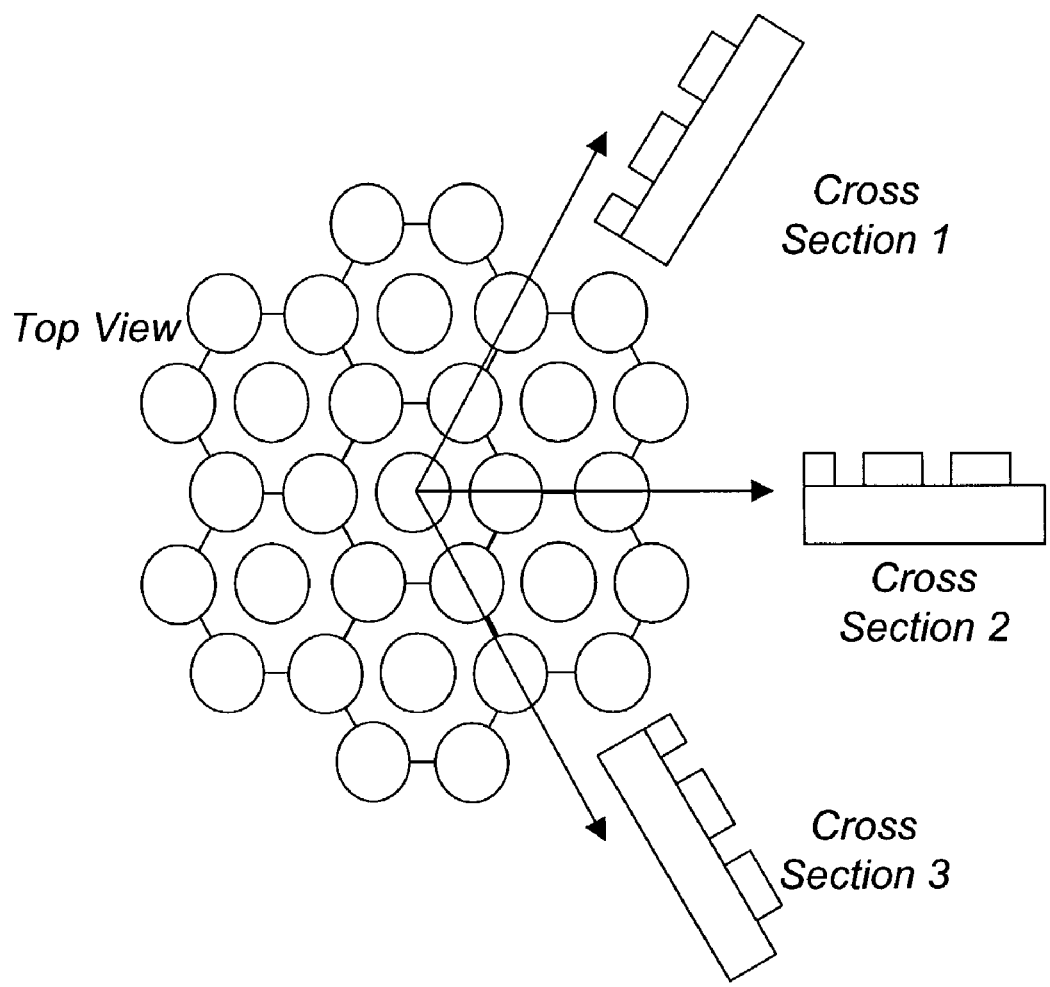
FIG. 18 shows a grid structure comprising a hexagonal grid of holes (or a hexagonal grid of posts) that closely approximates the concentric circle structure of FIG. 17 without requiring the illumination beam to be centered upon any particular location of the grid.

In another embodiment, an array of holes or posts are arranged to closely approximate the concentric circle structure described above without requiring the illumination beam to be centered upon any particular location of the grid. See e.g. FIG. 18. Such an array pattern is automatically generated by the optical interference of three laser beams incident on a surface from three directions at equal angles. In this pattern, the holes (or posts) are centered upon the corners of an array of closely packed hexagons as shown in FIG. 18. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

Another grating that can be produced using the methods of the invention is a volume surface-relief volume diffractive grating (a SRVD grating), also referred to as a three-dimensional grating. SRVD gratings have a surface that reflects predominantly at a particular narrow band of optical wavelengths when illuminated with a broad band of optical wavelengths. Where specific binding substances and/or binding partners are immobilized on a SRVD grating, producing a SRVD biosensor, the reflected narrow band of wavelengths of light is shifted. One-dimensional surfaces, such as thin film interference filters and Bragg reflectors, can select a narrow range of reflected or transmitted wavelengths from a broadband excitation source, however, the deposition of additional material, such as specific binding substances and/or binding partners onto their upper surface results only in a change in the resonance linewidth, rather than the resonance wavelength. In contrast, SRVD biosensors have the ability to alter the reflected wavelength with the addition of material, such as specific binding substances and/or binding partners to the surface. The depth and period of relief volume diffraction structures are less than the resonance wavelength of light reflected from a biosensor.

A three-dimensional surface-relief volume diffractive grating can be, for example, a three-dimensional phase-quantized terraced surface relief pattern whose groove pattern resembles a stepped pyramid. When such a grating is illuminated by a beam of broadband radiation, light will be coherently reflected from the equally spaced terraces at a wavelength given by twice the step spacing times the index of refraction of the surrounding medium. Light of a given wavelength is resonantly diffracted or reflected from the steps that are a half-wavelength apart, and with a bandwidth that is inversely proportional to the number of steps. The reflected or diffracted color can be controlled by the deposition of a high refractive index layer so that a new wavelength is selected, depending on the index of refraction of the coating. As an example, a thin-film layer of zinc sulfide, titanium dioxide, tantalum oxide, or silicon nitride can be sputter deposited onto the grating.

Figure 20:
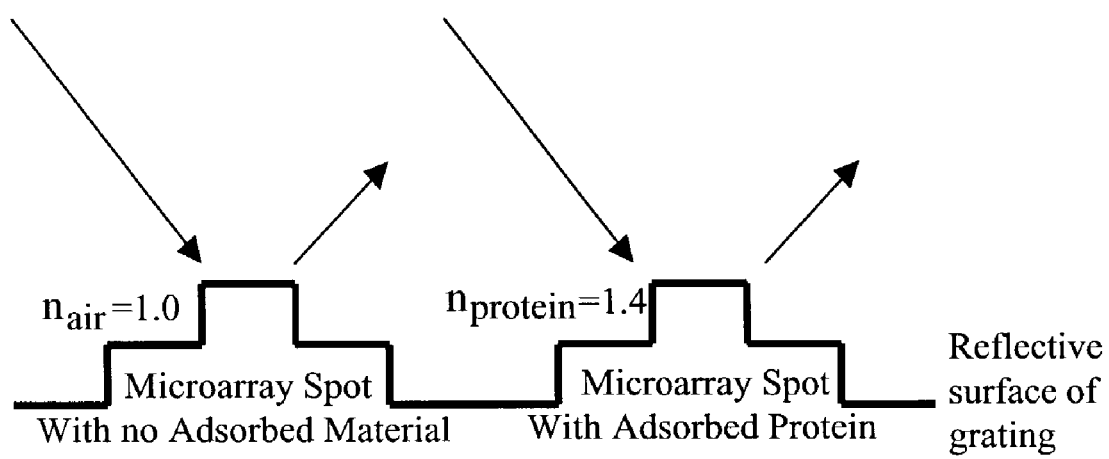
FIG. 20 shows a graphic representation of how adsorbed material, such as a protein monolayer, will increase the reflected wavelength of a biosensor that comprises a three-dimensional grating.

An example of a three-dimensional phase-quantized terraced surface relief pattern is a pattern that resembles a stepped pyramid. Each inverted pyramid is approximately 1 micron in diameter, preferably, each inverted pyramid can be about 0.5 to about 5 microns diameter, including for example, about 1 micron. The pyramid structures can be close-packed so that a typical microarray spot with a diameter of about 150–200 microns can incorporate several hundred stepped pyramid structures. The relief volume diffraction structures have a period of about 0.1 to about 1 micron and a depth of about 0.1 to about 1 micron. FIG. 20 demonstrates how individual microarray locations (with an entire microarray spot incorporating hundreds of pyramids now represented by a single pyramid for one microarray spot) can be optically queried to determine if specific binding substances or binding partners are adsorbed onto the surface. When the biosensor is illuminated with white light, pyramid structures without significant bound material will reflect wavelengths determined by the step height of the pyramid structure. When higher refractive index material, such as binding partners or specific binding substances, are incorporated over the reflective metal surface, the reflected wavelength is modified to shift toward longer wavelengths. The color that is reflected from the terraced step structure is theoretically given as twice the step height times the index of refraction of a reflective material that is coated onto the first surface of a sheet material of a SRVD biosensor. A reflective material can be, for example silver, aluminum, or gold.

One or more specific binding substances, as described above, are immobilized on the reflective material of a SRVD biosensor. One or more specific binding substances can be arranged in microarray of distinct locations, as described above, on the reflective material.

Because the reflected wavelength of light from a SRVD biosensor is confined to a narrow bandwidth, very small changes in the optical characteristics of the surface manifest themselves in easily observed changes in reflected wavelength spectra. The narrow reflection bandwidth provides a surface adsorption sensitivity advantage compared to reflectance spectrometry on a flat surface.

A SRVD biosensor reflects light predominantly at a first single optical wavelength when illuminated with a broad band of optical wavelengths, and reflects light at a second single optical wavelength when one or more specific binding substances are immobilized on the reflective surface. The reflection at the second optical wavelength results from optical interference. A SRVD biosensor also reflects light at a third single optical wavelength when the one or more specific binding substances are bound to their respective binding partners, due to optical interference.

Readout of the reflected color can be performed serially by focusing a microscope objective onto individual microarray spots and reading the reflected spectrum, or in parallel by, for example, projecting the reflected image of the microarray onto a high resolution color CCD camera.

In one embodiment of the invention, an optical device is provided. An optical device comprises a structure similar to a biosensor of the invention; however, an optical device does not comprise one of more binding substances immobilized on the grating. An optical device can be used as, for example, a narrow band optical filter.

Specific Binding Substances and Binding Partners

One or more specific binding substances can be immobilized on colorimetric resonant reflectance gratings produced by the methods of the invention by for example, physical adsorption or by chemical binding where a specific binding substance is bound to a colorimetric resonant reflectance grating, to produce a biosensor. A specific binding substance can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, or biological sample. A biological sample can be for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, or prostatite fluid.

Preferably, one or more specific binding substances are arranged in a microarray of distinct locations on a biosensor. A microarray of specific binding substances comprises one or more specific binding substances on a surface of a biosensor such that a surface contains many distinct locations, each with a different specific binding substance or with a different amount of a specific binding substance. For example, an array can comprise 1, 10, 100, 1,000, 10,000, or 100,000 distinct locations. Such a biosensor surface is called a microarray because one or more specific binding substances are typically laid out in a regular grid pattern in x-y coordinates. However, a microarray of the invention can comprise one or more specific binding substances laid out in any type of regular or irregular pattern. For example, distinct locations can define a microarray of spots of one or more specific binding substances. A microarray spot can be about 50 to about 500 microns in diameter. A microarray spot can also be about 150 to about 200 microns in diameter. One or more specific binding substances can be bound to their specific binding partners.

A microarray on a biosensor of the invention can be created by placing microdroplets of one or more specific binding substances onto, for example, an x-y grid of locations on an optical grating or cover layer surface. When the biosensor is exposed to a test sample comprising one or more binding partners, the binding partners will be preferentially attracted to distinct locations on the microarray that comprise specific binding substances that have high affinity for the binding partners. Some of the distinct locations will gather binding partners onto their surface, while other locations will not.

A specific binding substance specifically binds to a binding partner that is added to the surface of a biosensor of the invention. A specific binding substance specifically binds to its binding partner, but does not substantially bind other binding partners added to the surface of a biosensor. For example, where the specific binding substance is an antibody and its binding partner is a particular antigen, the antibody specifically binds to the particular antigen, but does not substantially bind other antigens. A binding partner can be, for example, a nucleic acid, polypeptide, antigen, polyclonal antibody, monoclonal antibody, single chain antibody (scFv), F(ab) fragment, F(ab')$_2$ fragment, Fv fragment, small organic molecule, cell, virus, bacteria, and biological sample. A biological sample can be, for example, blood, plasma, serum, gastrointestinal secretions, homogenates of tissues or tumors, synovial fluid, feces, saliva, sputum, cyst fluid, amniotic fluid, cerebrospinal fluid, peritoneal fluid, lung lavage fluid, semen, lymphatic fluid, tears, and prostatite fluid.

One example of a microarray of the invention is a nucleic acid microarray, in which each distinct location within the array contains a different nucleic acid molecule. In this embodiment, the spots within the nucleic acid microarray detect complementary chemical binding with an opposing strand of a nucleic acid in a test sample.

While microtiter plates are the most common format used for biochemical assays, microarrays are increasingly seen as a means for maximizing the number of biochemical interactions that can be measured at one time while minimizing the volume of precious reagents. By application of specific binding substances with a microarray spotter onto a biosensor of the invention, specific binding substance densities of 10,000 specific binding substances/in$^2$ can be obtained. By focusing an illumination beam to interrogate a single microarray location, a biosensor can be used as a label-free microarray readout system. A microarray can also be illuminated by a line scanner, wherein an entire line or row of microarray locations are illuminated at once. A CCD camera can also be used to scan a microarray. A CCD camera comprises an array of photosensitive elements upon which the microarray image is projected. The value of each pixel represents the light intensity for the corresponding area of the microarray. The result of scanning the microarray is the production of is one or more 2-dimensional images. The images are analyzed to determine the extent of binding to the microarray.

Immobilization of One or More Specific Binding Substances

Immobilization of one or more binding substances onto a biosensor is performed so that a specific binding substance will not be washed away by rinsing procedures, and so that its binding to binding partners in a test sample is unimpeded by the biosensor surface. Several different types of surface chemistry strategies have been implemented for covalent attachment of specific binding substances to, for example, glass for use in various types of microarrays and biosensors. See, e.g., FIG. 8. These same methods can be readily adapted to a biosensor of the invention. Surface preparation of a biosensor so that it contains the correct functional groups for binding one or more specific binding substances is an integral part of the biosensor manufacturing process.

One or more specific binding substances can be attached to a biosensor surface by physical adsorption (i.e., without the use of chemical linkers) or by chemical binding (i.e., with the use of chemical linkers). Chemical binding can generate stronger attachment of specific binding substances on a biosensor surface and provide defined orientation and conformation of the surface-bound molecules.

Liquid-Containing Vessels

Figure 10:
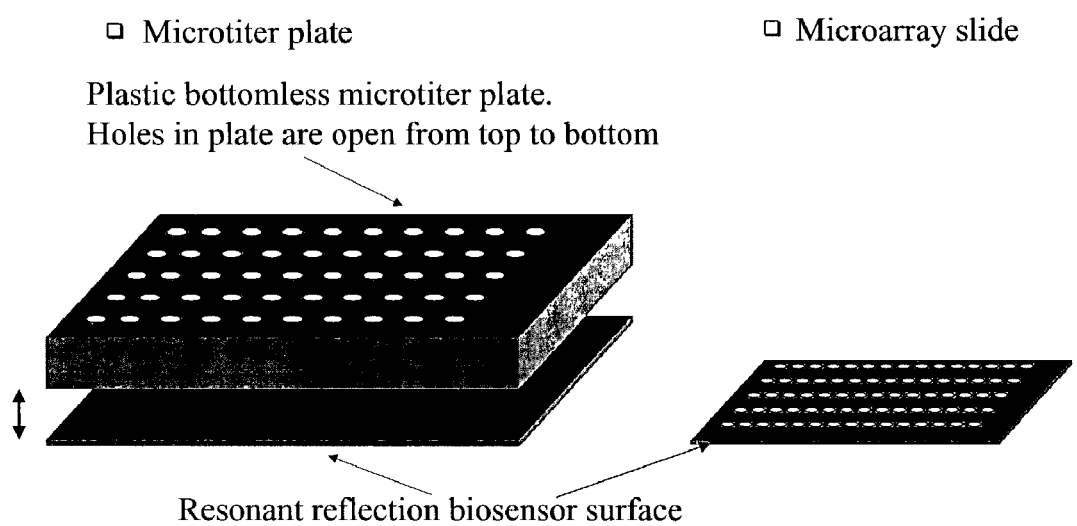
FIGS. 10A–B shows two biosensor formats that can incorporate a colorimetric resonant reflectance biosensor.

A grating of the invention can comprise an inner surface, for example, a bottom surface of a liquid-containing vessel. A liquid-containing vessel can be, for example, a microtiter plate well, a test tube, a petri dish, or a microfluidic channel. One embodiment of this invention is a biosensor that is incorporated into any type of microtiter plate. For example, a biosensor can be incorporated into the bottom surface of a microtiter plate by assembling the walls of the reaction vessels over the resonant reflection surface, as shown in FIG. 10A and 10B, so that each reaction "spot" can be exposed to a distinct test sample. Therefore, each individual microtiter plate well can act as a separate reaction vessel. Separate chemical reactions can, therefore, occur within adjacent wells without intermixing reaction fluids and chemically distinct test solutions can be applied to individual wells.

Several methods for attaching a biosensor or grating of the invention to the bottom surface of bottomless microtiter plates can be used, including, for example, adhesive attachment, ultrasonic welding, and laser welding.

The most common assay formats for pharmaceutical high-throughput screening laboratories, molecular biology research laboratories, and diagnostic assay laboratories are microtiter plates. The plates are standard-sized plastic cartridges that can contain 96, 384, or 1536 individual reaction vessels arranged in a grid. Due to the standard mechanical configuration of these plates, liquid dispensing, robotic plate handling, and detection systems are designed to work with this common format. A biosensor of the invention can be incorporated into the bottom surface of a standard microtiter plate. See, e g., FIG. 10A. Because the biosensor surface can be fabricated in large areas, and because the readout system does not make physical contact with the biosensor surface, an arbitrary number of individual biosensor areas can be defined that are only limited by the focus resolution of the illumination optics and the x-y stage that scans the illumination/detection probe across the biosensor surface.

Methods of using Biosensors

Biosensors can be used to study one or a number of specific binding substance/binding partner interactions in parallel. Binding of one or more specific binding substances to their respective binding partners can be detected, without the use of labels, by applying one or more binding partners to a biosensor that have one or more specific binding substances immobilized on their surfaces. A biosensor is illuminated with light and a maxima in reflected wavelength, or a minima in transmitted wavelength of light is detected from the biosensor. If one or more specific binding substances have bound to their respective binding partners, then the reflected wavelength of light is shifted as compared to a situation where one or more specific binding substances have not bound to their respective binding partners. Where a biosensor is coated with an array of distinct locations containing the one or more specific binding substances, then a maxima in reflected wavelength or minima in transmitted wavelength of light is detected from each distinct location of the biosensor.

Figure 9:
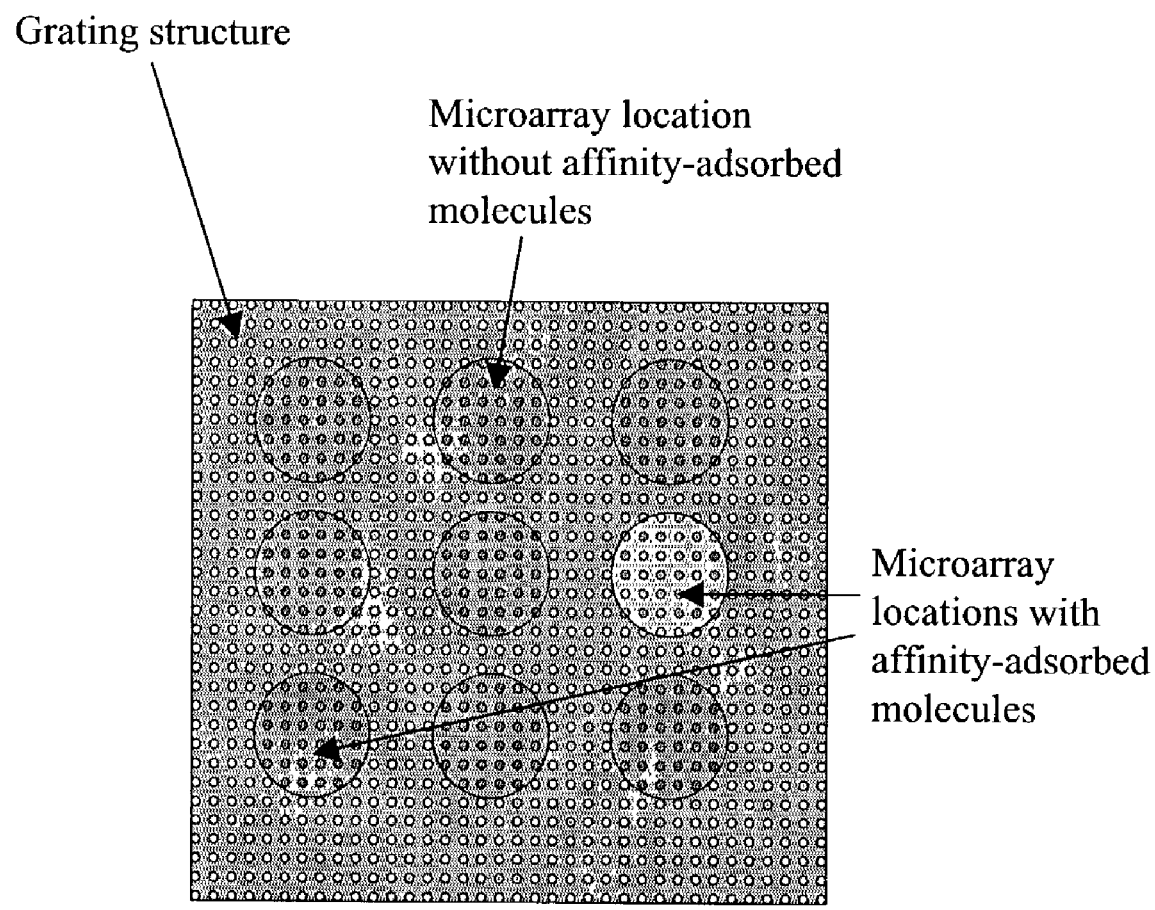
FIG. 9 shows an example of a biosensor used as a microarray.
Figure 11:
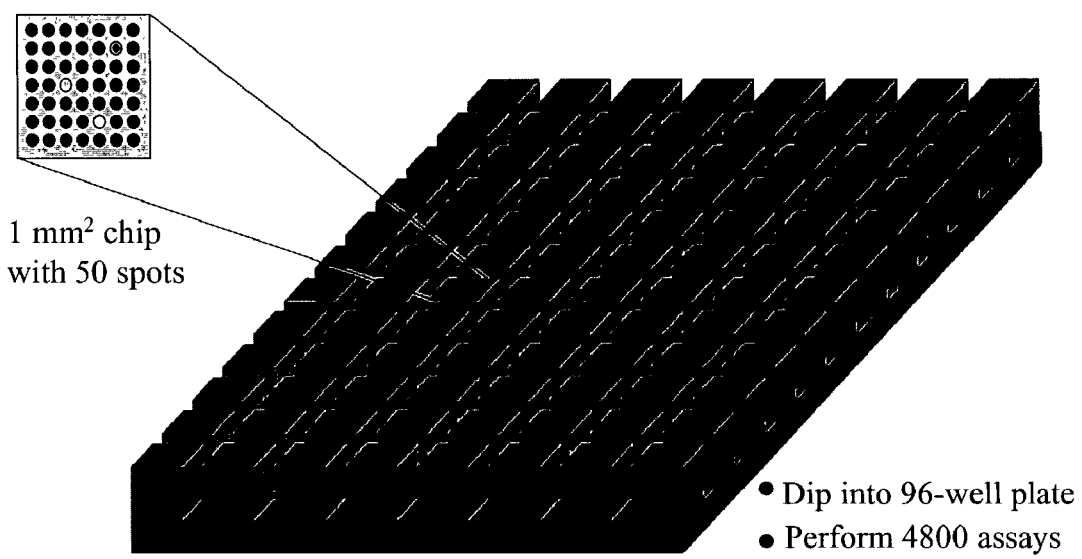
FIG. 11 shows an array of arrays concept for using a biosensor platform to perform assays with higher density and throughput.
Figure 12:
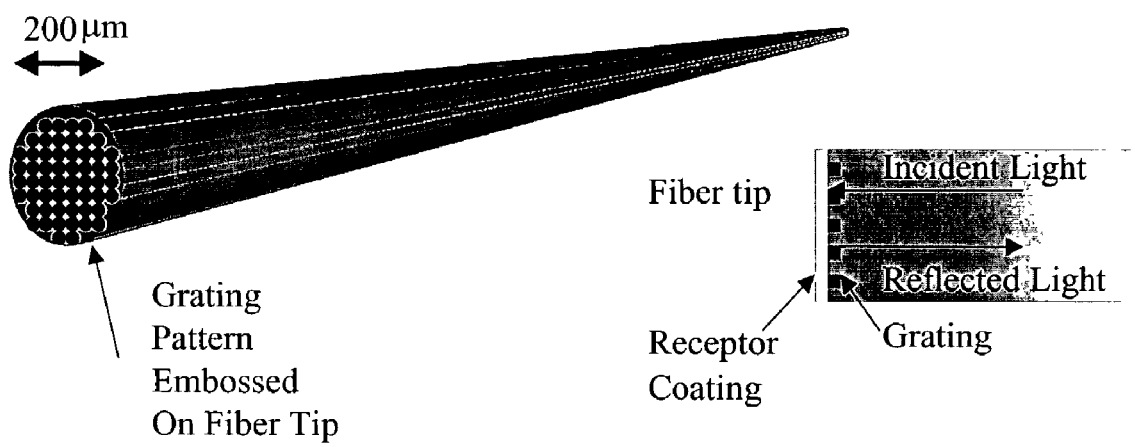
FIG. 12 demonstrates an example of a biosensor that occurs on the tip of a fiber probe for in vivo detection of biochemical substances.

In one embodiment of the invention, a variety of specific binding substances, for example, antibodies, can be immobilized in an array format onto a biosensor of the invention. See, e.g., FIG. 9. The biosensor is then contacted with a test sample of interest comprising binding partners, such as proteins. Only the proteins that specifically bind to the antibodies immobilized on the biosensor remain bound to the biosensor. Such an approach is essentially a large-scale version of an enzyme-linked immunosorbent assay; however, the use of an enzyme or fluorescent label is not required. For high-throughput applications, biosensors can be arranged in an array of arrays, wherein several biosensors comprising an array of specific binding substances are arranged in an array. See, e.g., FIG. 11. Such an array of arrays can be, for example, dipped into microtiter plate to perform many assays at one time. In another embodiment, a biosensor can occur on the tip of a fiber probe for in vivo detection of biochemical substance. See, FIG. 12.

The activity of an enzyme can be detected by applying one or more enzymes to a biosensor to which one or more specific binding substances have been immobilized. The biosensor is washed and illuminated with light. The reflected wavelength of light is detected from the biosensor. Where the one or more enzymes have altered the one or more specific binding substances of the biosensor by enzymatic activity, the reflected wavelength of light is shifted.

Additionally, a test sample, for example, cell lysates containing binding partners can be applied to a biosensor of the invention, followed by washing to remove unbound material. The binding partners that bind to a biosensor can be eluted from the biosensor and identified by, for example, mass spectrometry. Optionally, a phage DNA display library can be applied to a biosensor of the invention followed by washing to remove unbound material. Individual phage particles bound to the biosensor can be isolated and the inserts in these phage particles can then be sequenced to determine the identity of the binding partner.

For the above applications, and in particular proteomics applications, the ability to selectively bind material, such as binding partners from a test sample onto a biosensor of the invention, followed by the ability to selectively remove bound material from a distinct location of the biosensor for further analysis is advantageous. Biosensors of the invention are also capable of detecting and quantifying the amount of a binding partner from a sample that is bound to a biosensor array distinct location by measuring the shift in reflected wavelength of light. For example, the wavelength shift at one distinct biosensor location can be compared to positive and negative controls at other distinct biosensor locations to determine the amount of a binding partner that is bound to a biosensor array distinct location.

Detection Systems

A detection system can comprise a biosensor a light source that directs light to the biosensor, and a detector that detects light reflected from the biosensor. In one embodiment, it is possible to simplify the readout instrumentation by the application of a filter so that only positive results over a determined threshold trigger a detection.

A light source can illuminate a biosensor from its top surface, i.e., the surface to which one or more specific binding substances are immobilized or from its bottom surface. By measuring the shift in resonant wavelength at each distinct location of a biosensor of the invention, it is possible to determine which distinct locations have binding partners bound to them. The extent of the shift can be used to determine the amount of binding partners in a test sample and the chemical affinity between one or more specific binding substances and the binding partners of the test sample.

A biosensor can be illuminated twice. The first measurement determines the reflectance spectra of one or more distinct locations of a biosensor array with one or more specific binding substances immobilized on the biosensor. The second measurement determines the reflectance spectra after one or more binding partners are applied to a biosensor. The difference in peak wavelength between these two measurements is a measurement of the amount of binding partners that have specifically bound to a biosensor or one or more distinct locations of a biosensor. This method of illumination can control for small nonuniformities in a surface of a biosensor that can result in regions with slight variations in the peak resonant wavelength. This method can also control for varying concentrations or molecular weights of specific binding substances immobilized on a biosensor.

Computer simulation can be used to determine the expected dependence between a peak resonance wavelength and an angle of incident illumination. The substrate chosen was glass ($n_{substrate}$=1.50). The grating is an optical pattern of silicon nitride squares ($t_2$=180 nm, $n_2$=2.01 (n=refractive index)), $k_2$=0.001 (k=absorption coefficient)) with a period of 510 nm, and a filling factor of 56.2% (i.e., 56.2% of the surface is covered with silicon nitride squares while the rest is the area between the squares). The areas between silicon nitride squares are filled with a lower refractive index material. The same material also covers the squares and provides a uniformly flat upper surface. For this simulation, a glass layer was selected ($n_1$=1.40) that covers the silicon nitride squares by $t_2$=100 nm.

The reflected intensity as a function of wavelength was modeled using GSOLVER software, which utilizes full 3-dimensional vector code using hybrid Rigorous Coupled Wave Analysis and Modal analysis. GSOLVER calculates diffracted fields and diffraction efficiencies from plane wave illumination of arbitrarily complex grating structures. The illumination can be from any incidence and any polarization.

Figure 14:
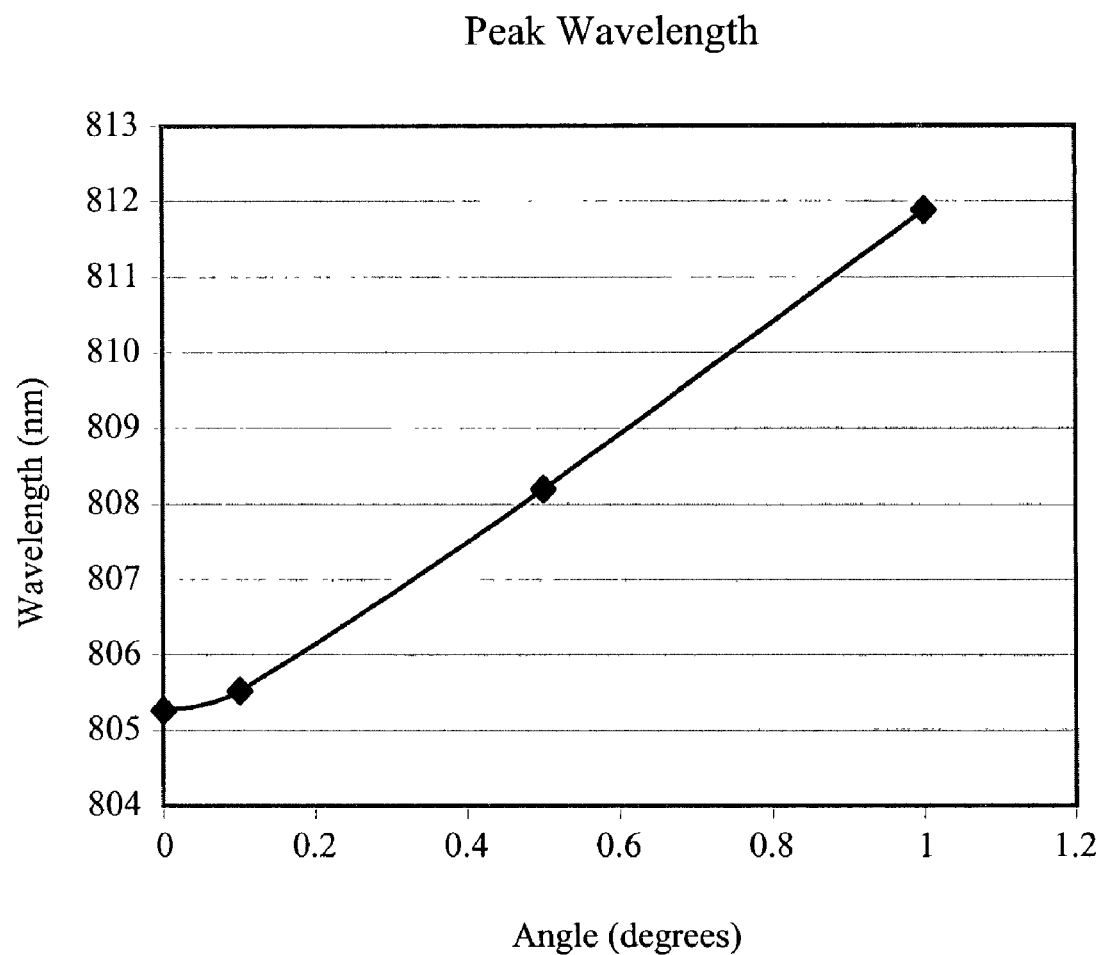
FIG. 14 shows resonance wavelength of a biosensor as a function of incident angle of detection beam.

FIG. 14 plots the dependence of the peak resonant wavelength upon the incident illumination angle. The simulation shows that there is a strong correlation between the angle of incident light, and the peak wavelength that is measured. This result implies that the collimation of the illuminating beam, and the alignment between the illuminating beam and the reflected beam will directly affect the resonant peak linewidth that is measured. If the collimation of the illuminating beam is poor, a range illuminating angles will be incident on the biosensor surface, and a wider resonant peak will be measured than if purely collimated light were incident.

Because the lower sensitivity limit of a biosensor is related to the ability to determine the peak maxima, it is important to measure a narrow resonant peak. Therefore, the use of a collimating illumination system with the biosensor provides for the highest possible sensitivity.

One type of detection system for illuminating the biosensor surface and for collecting the reflected light is a probe containing, for example, six illuminating optical fibers that are connected to a light source, and a single collecting optical fiber connected to a spectrometer. The number of fibers is not critical, any number of illuminating or collecting fibers are possible. The fibers are arranged in a bundle so that the collecting fiber is in the center of the bundle, and is surrounded by the six illuminating fibers. The tip of the fiber bundle is connected to a collimating lens that focuses the illumination onto the surface of the biosensor.

In this probe arrangement, the illuminating and collecting fibers are side-by-side. Therefore, when the collimating lens is correctly adjusted to focus light onto the biosensor surface, one observes six clearly defined circular regions of illumination, and a central dark region. Because the biosensor does not scatter light, but rather reflects a collimated beam, no light is incident upon the collecting fiber, and no resonant signal is observed. Only by defocusing the collimating lens until the six illumination regions overlap into the central region is any light reflected into the collecting fiber. Because only defocused, slightly uncollimated light can produce a signal, the biosensor is not illuminated with a single angle of incidence, but with a range of incident angles. The range of incident angles results in a mixture of resonant wavelengths due to the dependence shown in FIG. 14. Thus, wider resonant peaks are measured than might otherwise be possible.

Figure 13:
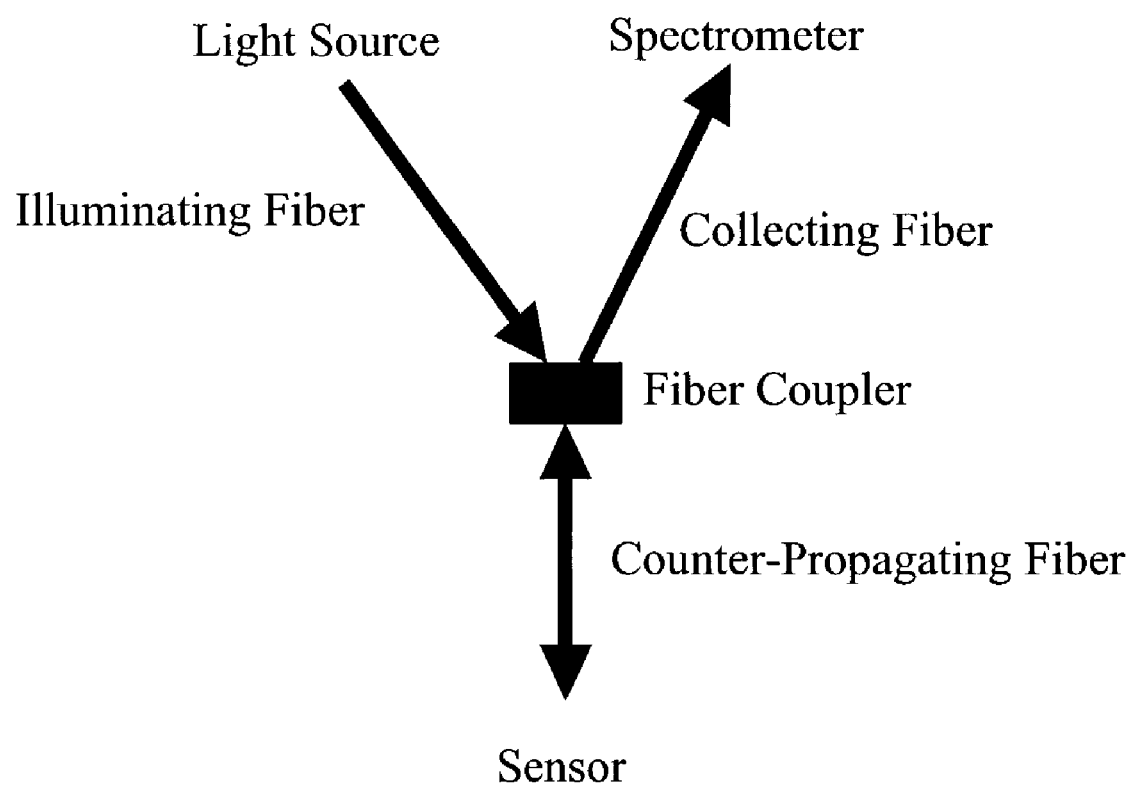
FIG. 13 shows an example of the use of two coupled fibers to illuminate and collect reflected light from a biosensor.

Therefore, it is desirable for the illuminating and collecting fiber probes to spatially share the same optical path. Several methods can be used to co-locate the illuminating and collecting optical paths. For example, a single illuminating fiber, which is connected at its first end to a light source that directs light at the biosensor, and a single collecting fiber, which is connected at its first end to a detector that detects light reflected from the biosensor, can each be connected at their second ends to a third fiber probe that can act as both an illuminator and a collector. The third fiber probe is oriented at a normal angle of incidence to the biosensor and supports counter-propagating illuminating and reflecting optical signals. An example of such a detection system is shown in FIG. 13.

Figure 15:
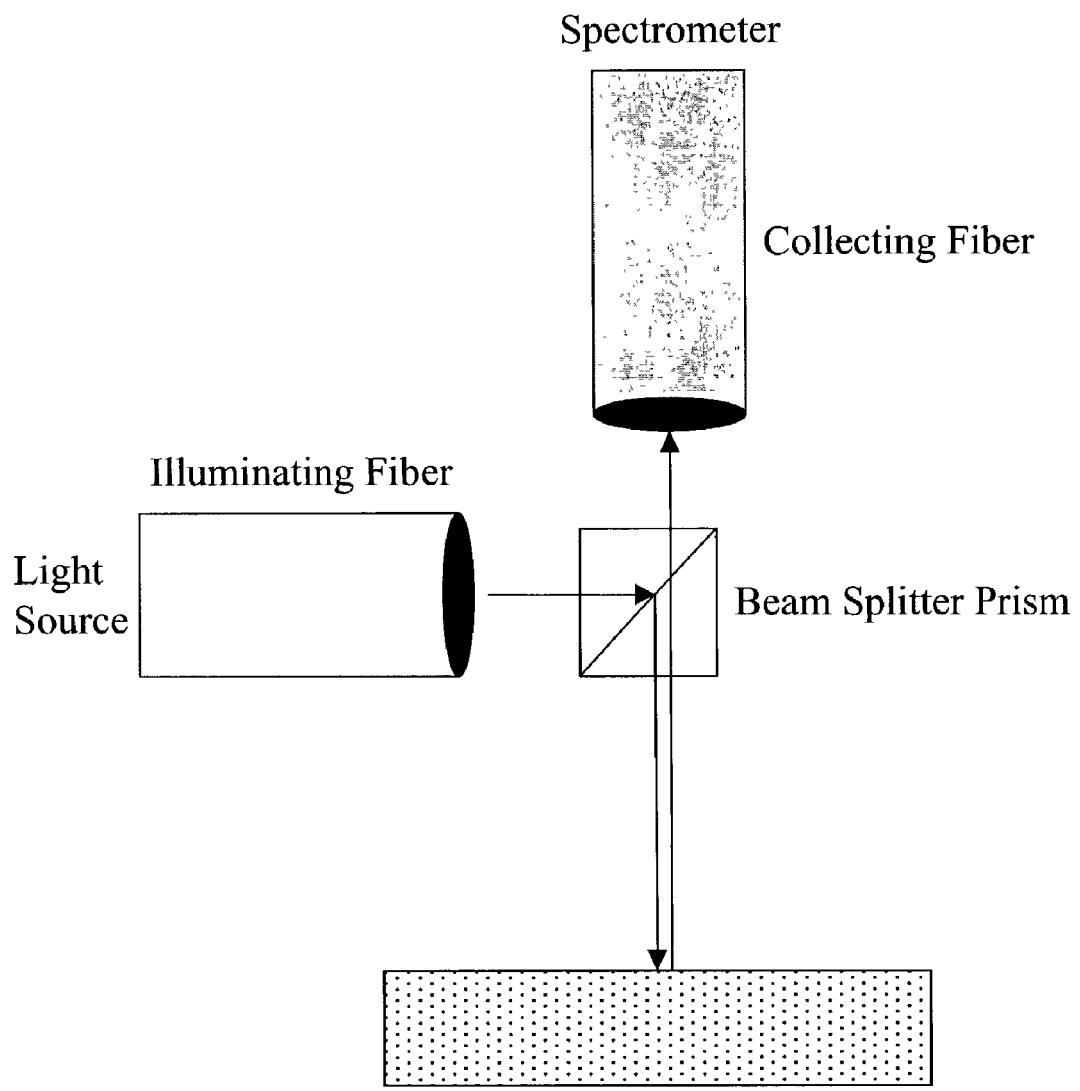
FIG. 15 shows an example of the use of a beam splitter to enable illuminating and reflected light to share a common collimated optical path to a biosensor.

Another method of detection involves the use of a beam splitter that enables a single illuminating fiber, which is connected to a light source, to be oriented at a 90 degree angle to a collecting fiber, which is connected to a detector. Light is directed through the illuminating fiber probe into the beam splitter, which directs light at the biosensor. The reflected light is directed back into the beam splitter, which directs light into the collecting fiber probe. An example of such a detection device is shown in FIG. 15. A beam splitter allows the illuminating light and the reflected light to share a common optical path between the beam splitter and the biosensor, so perfectly collimated light can be used without defocusing.

Angular Scanning

Detection systems of the invention are based on collimated white light illumination of a biosensor surface and optical spectroscopy measurement of the resonance peak of the reflected beam. Molecular binding on the surface of a biosensor is indicated by a shift in the peak wavelength value, while an increase in the wavelength corresponds to an increase in molecular absorption.

As shown in theoretical modeling and experimental data, the resonance peak wavelength is strongly dependent on the incident angle of the detection light beam. FIG. 14 depicts this dependence as modeled for a biosensor of the invention. Because of the angular dependence of the resonance peak wavelength, the incident white light needs to be well collimated. Angular dispersion of the light beam broadens the resonance peak, and reduces biosensor detection sensitivity. In addition, the signal quality from the spectroscopic measurement depends on the power of the light source and the sensitivity of the detector. In order to obtain a high signal-to-noise ratio, an excessively long integration time for each detection location can be required, thus lengthening overall time to readout a biosensor plate. A tunable laser source can be used for detection of grating resonance, but is expensive.

In one embodiment of the invention, these disadvantages are addressed by using a laser beam for illumination of a biosensor, and a light detector for measurement of reflected beam power. A scanning mirror device can be used for varying the incident angle of the laser beam, and an optical system is used for maintaining collimation of the incident laser beam. See, e.g., "Optical Scanning" (Gerald F. Marchall ed., Marcel Dekker (1991). Any type of laser scanning can be used. For example, a scanning device that can generate scan lines at a rate of about 2 lines to about 1,000 lines per second is useful in the invention. In one embodiment of the invention, a scanning device scans from about 50 lines to about 300 lines per second.

Figure 16:
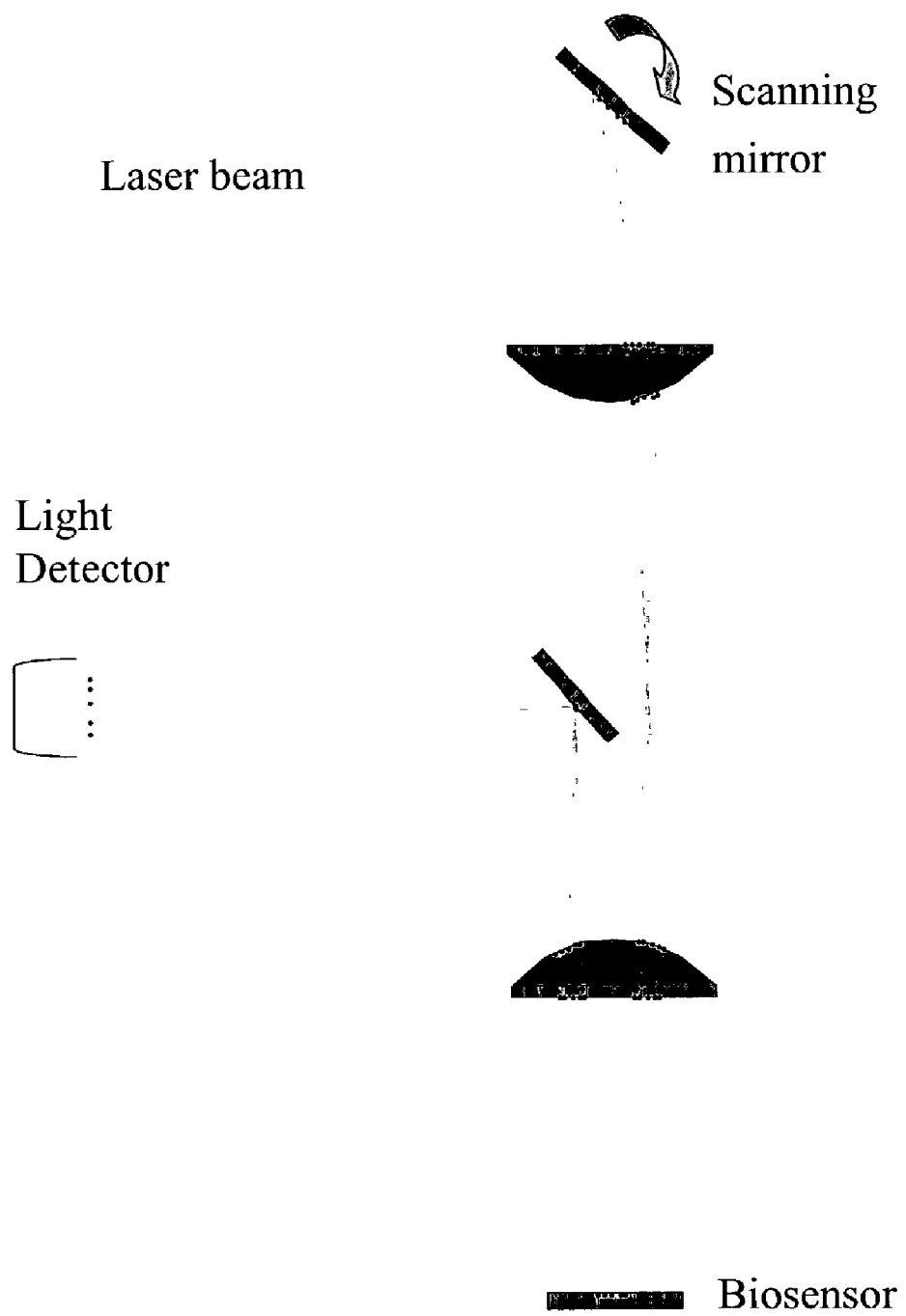
FIG. 16 shows an example of a system for angular scanning of a biosensor.
Figure 19:
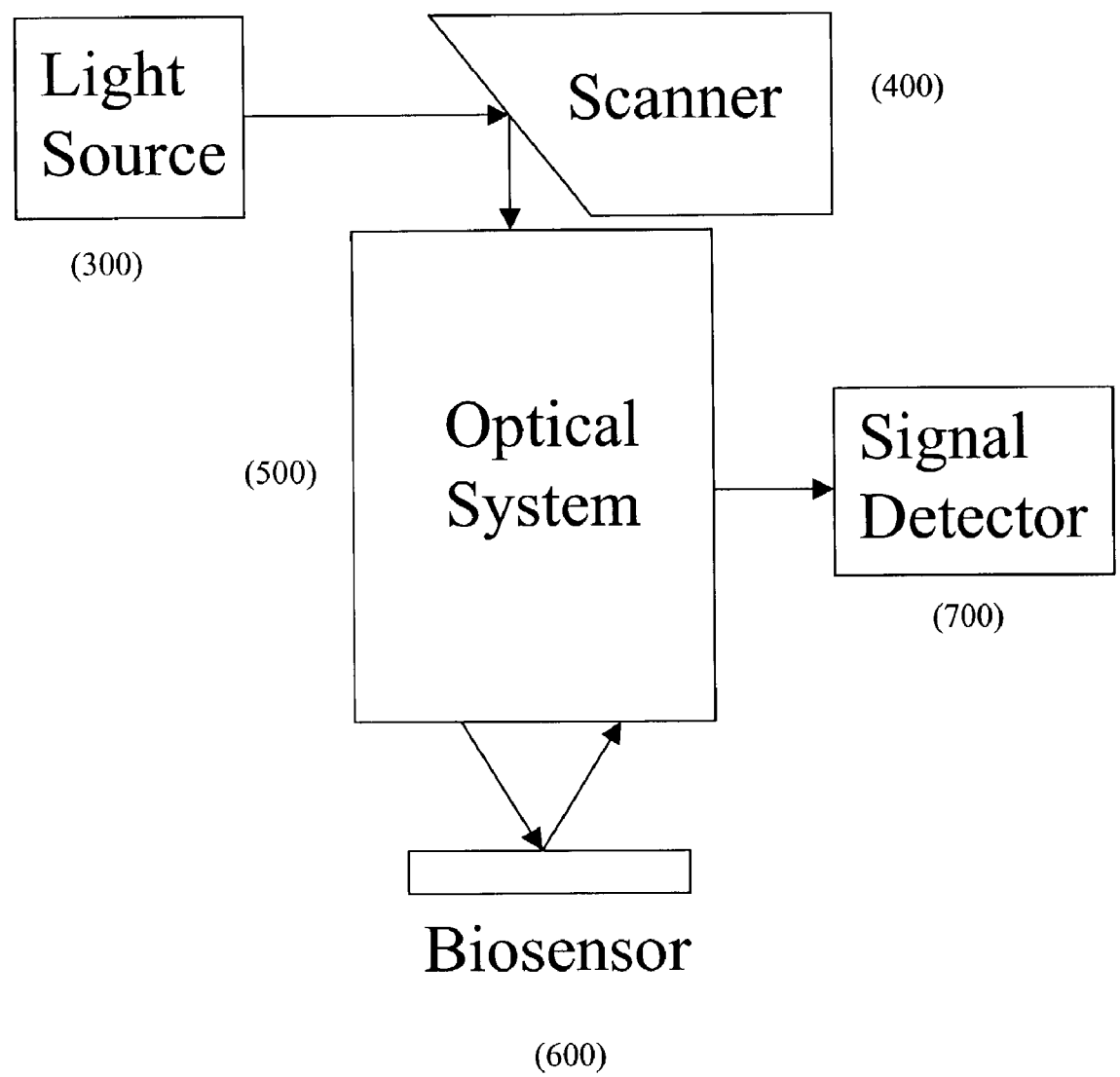
FIG. 19 shows a schematic diagram of a detection system.

In one embodiment, the reflected light beam passes through part of the laser scanning optical system, and is measured by a single light detector. The laser source can be a diode laser with a wavelength of, for example, 780 nm, 785 nm, 810 nm, or 830 nm. Laser diodes such as these are readily available at power levels up to 150 mW, and their wavelengths correspond to high sensitivity of Si photodiodes. The detector thus can be based on photodiode biosensors. An example of such a detection system is shown in FIG. 19. A light source (300) provides light to a scanner device (400), which directs the light into an optical system (500). The optical system (500) directs light to a biosensor (600). Light is reflected from the biosensor (600) to the optical system (500), which then directs the light into a light signal detector (700). One embodiment of a detection system is shown in FIG. 16, which demonstrates that while the scanning mirror changes its angular position, the incident angle of the laser beam on the surface changes by nominally twice the mirror angular displacement. The scanning mirror device can be a linear galvanometer, operating at a frequency of about 2 Hz up to about 120 Hz, and mechanical scan angle of about 10 degrees to about 20 degrees. In this example, a single scan can be completed within about 10 msec. A resonant galvanometer or a polygon scanner can also be used. The example shown in FIG. 16 includes a simple optical system for angular scanning. It consists of a pair of lenses with a common focal point between them. The optical system can be designed to achieve optimized performance for laser collimation and collection of reflected light beam.

The angular resolution depends on the galvanometer specification, and reflected light sampling frequency. Assuming galvanometer resolution of 30 arcsec mechanical, corresponding resolution for biosensor angular scan is 60 arcsec, i.e. 0.017 degree. In addition, assume a sampling rate of 100 ksamples/sec, and 20 degrees scan within 10 msec. As a result, the quantization step is 20 degrees for 1000 samples, i.e. 0.02 degree per sample. In this example, a resonance peak width of 0.2 degree, as shown by Peng and Morris (Experimental demonstration of resonant anomalies in diffraction from two-dimensional gratings, *Optics Lett.*, 21:549 (1996)), will be covered by 10 data points, each of which corresponds to resolution of the detection system.

The advantages of such a detection system includes: excellent collimation of incident light by a laser beam, high signal-to-noise ratio due to high beam power of a laser diode, low cost due to a single element light detector instead of a spectrometer, and high resolution of resonance peak due to angular scanning.

The following are provided for exemplification purposes only and are not intended to limit the scope of the invention described in broad terms above. All references cited in this disclosure are incorporated herein by reference.

EXAMPLE

A rigid master structure was etched into the surface of a silicon or glass wafer. PDMS (Polydimethylsiloxane) Sylgard 184 was poured over the master structure. See FIG. 1. The PDMS was prepared by mixing 10 parts PDMS to 1 part curing agent. Bubbles were removed by centrifugation at 3000 rpm for 30 seconds. The PDMS mixture was poured into a mold placed over the surface of the silicon or glass wafer. The PDMS mixture was cured into a flexible solid at 75° C. for four hours. The cured solid structure was peeled away from the rigid master structure.

Figure 2:
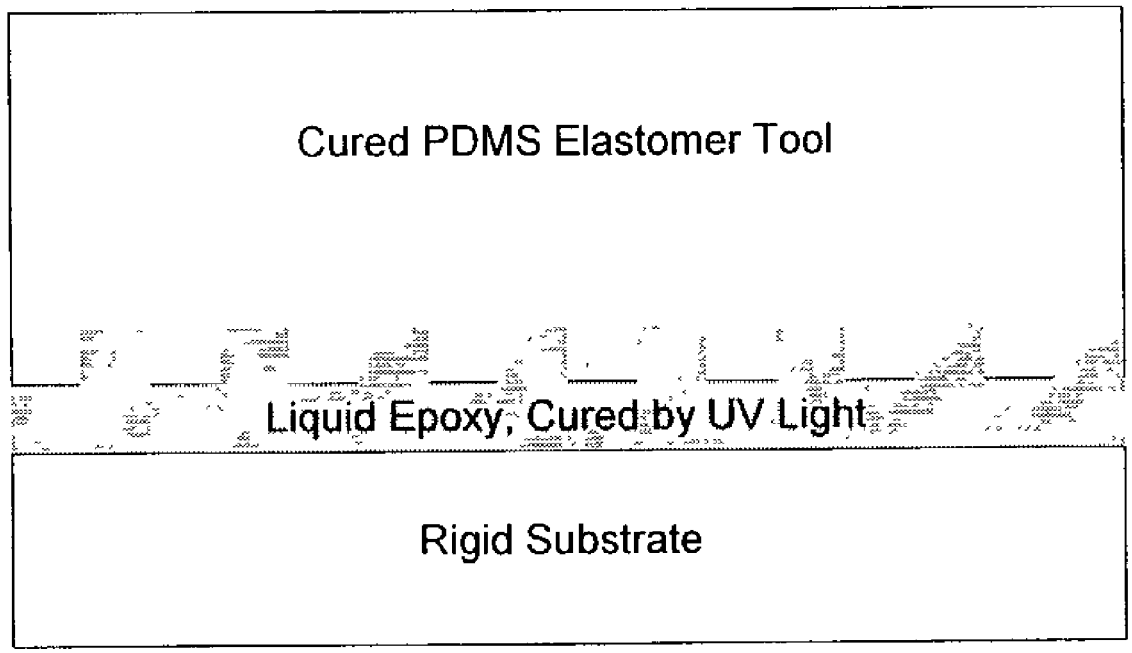
FIG. 2 demonstrates one embodiment of the invention wherein a flexible master structure is pressed into epoxy to generate a uniformly thin layer of epoxy between a substrate and a rigid master structure.
Figure 3:
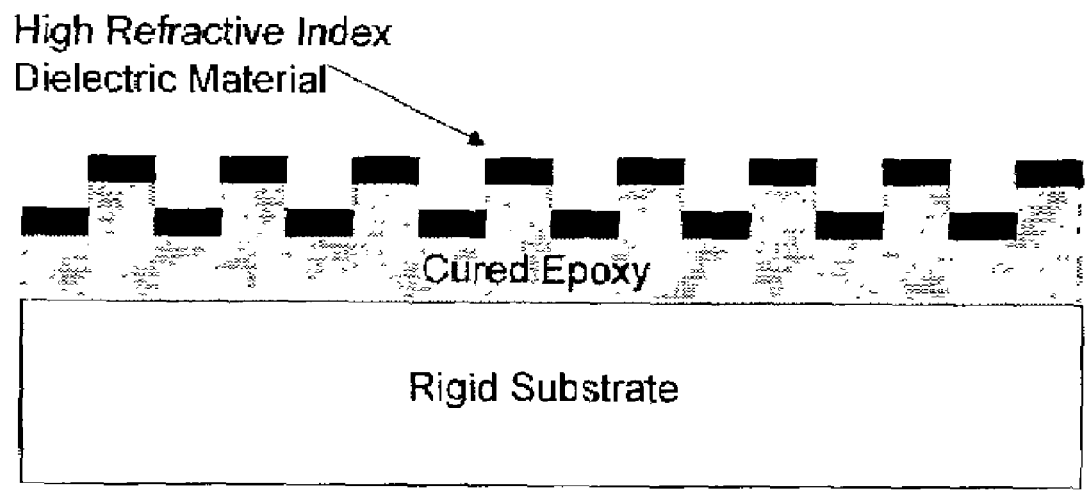
FIG. 3 demonstrates one embodiment of a structure of a colorimetric resonant reflection sensor fabricated using the methods of the invention.

An adhesion-enhancing thin film was applied to a glass substrate (Corning 1737 glass). The thin film was applied by dipping the glass substrate in hexamethyldisilane (HMDS) and drying with $N_2$. SU-8 epoxy (Summers Optical, Ft. Washington, Pa.) was applied to the substrate and the PDMS mold was pressed into the epoxy. A roller was used to press the mold into the epoxy to generate a uniformly thin layer of epoxy between the glass substrate and the PDMS mold. See FIG. 2. The epoxy was cured Xenon ultraviolet lamp for 95 seconds. The PDMS mold was peeled away from the glass substrate. A high refractive index dielectric thin film was deposited over the epoxy structure. See FIG. 3.

Figure 4:
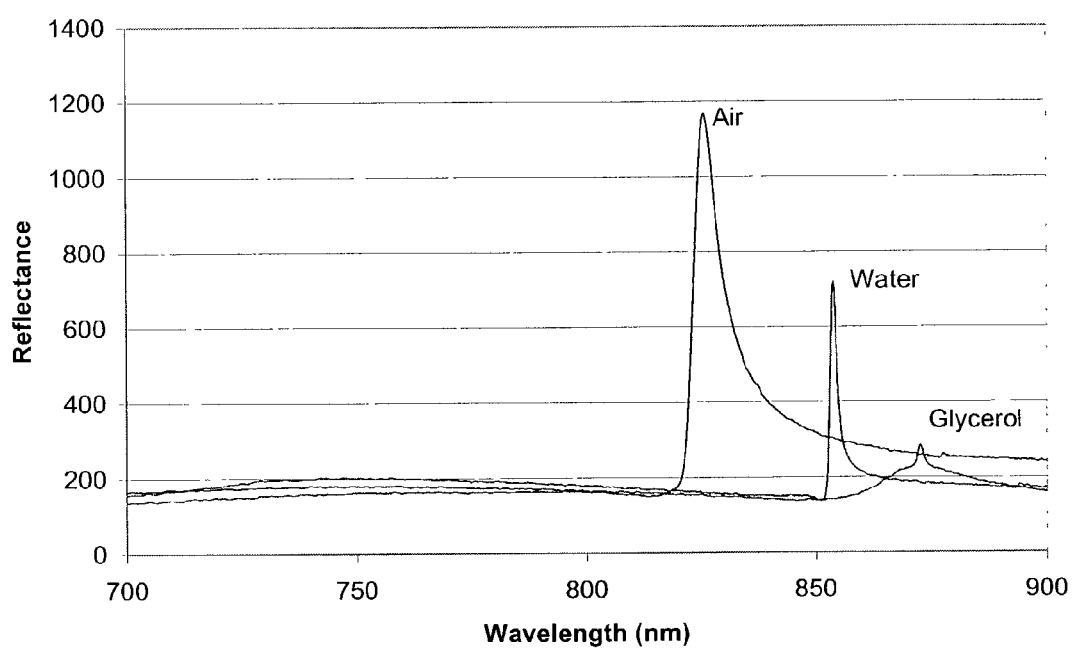
FIG. 4 shows the results when a colorimetric resonant reflection biosensor structure fabricated as described in Example 1 was illuminated with collimated white light. The expected resonant reflection peak spectra were obtained in air, water, and glycerol.

The colorimetric resonant reflection biosensor structure fabricated as described above was illuminated with collimated white light and the expected resonant reflection peak spectra (FIG. 4) were obtained in air, water, and glycerol. The peak wavelength value (PWV) shift between water and glycerol (refractive index change of $\Delta n=0.1424$) is 18.87 nm, indicating a shift coefficient of $\Delta PWV/\Delta n=138$. This sensor sensitivity is consistent with colorimetric resonant reflection biosensor structures produced by other methods.

We claim:

1. A method for fabrication of a colorimetric resonant reflection bio sensor structure comprising:
    (a) applying a liquid or semi-solid material that is capable of being transformed or cured into a flexible solid over a rigid master structure;
    (b) transforming the liquid or semi-solid material into a flexible master structure, wherein the flexible master structure has the rigid master structure embossed into a first surface of the flexible master structure;
    (c) peeling the flexible master structure from the rigid master structure;
    (d) placing the first surface of the flexible master structure onto a liquid or semi-solid layer, wherein the liquid or semi-solid layer is on a rigid substrate;
    (e) transforming or curing the liquid or semi-solid layer into a solid layer;
    (f) peeling the flexible master structure from the solid layer; and
    (g) applying a high refractive index dielectric film or reflective material over the solid layer,
    whereby a colorimetric resonant reflection biosensor structure is fabricated.

2. The method of claim 1, further comprising the step of immobilizing one or more specific binding substances to the high refractive index film or reflective material, whereby a colorimetric resonant reflection biosensor is fabricated.

3. The method of claim 1, wherein the rigid master structure is etched into the surface of a silicon or glass wafer.

4. The method of claim 1, wherein the liquid or semi-solid layer is epoxy, a polymer, a cement, a solvent free radiation addition polymerizable crosslinkable material or a resin.

5. The method of claim 4, wherein the crosslinkable material is an acrylate epoxy urethane based material.

6. The method of claim 1, wherein the liquid or semi-solid material is polydimethylsiloxane.

7. The method of claim 1, wherein an adhesion-enhancing thin film is placed between the liquid or semi-solid layer and the rigid substrate before the first surface of the flexible master structure is placed on the liquid or semi-solid layer.

8. The method of claim 1, wherein the rigid substrate is glass, plastic, polymer or epoxy.

9. The method of claim 1, wherein the liquid or semi-solid layer is transformed or cured by an electron beam, ultraviolet light or heat.

10. The method of claim 1, wherein the flexible master structure comprises a grating pattern selected from the group consisting of squares, triangles, sinusoidal waves, inverted "u" shapes, lines, circles, ellipses, trapezoids, ovals, rectangles, hexagons, phase-quantized terraced surface relief patterns whose groove pattern resembles a stepped pyramid, and concentric rings.

11. The method of claim 1, wherein the flexible master structure comprises a grating pattern having a periodic spacing of between about 0.1 microns to about 2.0 microns.

12. The method of claim 1, wherein the flexible master structure comprises a submicron grating pattern.

13. The method of claim 12, wherein the grating pattern has a periodic spacing of between about 0.2 microns to about 0.6 microns.

* * * * *